US012635062B2

(12) United States Patent (10) Patent No.: US 12,635,062 B2
Licht et al. (45) Date of Patent: May 19, 2026

(54) METHOD FOR GENERATING MICROWAVE-DRIVEN PLASMA

(71) Applicant: Direct Air Capture LLC, North Venice, FL (US)

(72) Inventors: Gad Licht, Venice, FL (US); Stuart Licht, Venice, FL (US)

(73) Assignee: Direct Air Capture LLC, North Venice, FL (US)

( * ) Notice: Subject to any disclaimer, the term of this patent is extended or adjusted under 35 U.S.C. 154(b) by 0 days.

(21) Appl. No.: 18/793,335

(22) Filed: Aug. 2, 2024

(65) Prior Publication Data

US 2026/0040426 A1 Feb. 5, 2026

(51) Int. Cl.
H05H 1/46 (2006.01)
A61L 2/14 (2006.01)
B08B 7/00 (2006.01)
*C25B 1/135* (2021.01)
*C25B 9/09* (2021.01)

(52) U.S. Cl.
CPC ............... H05H 1/461 (2021.05); A61L 2/14 (2013.01); B08B 7/0035 (2013.01); *C25B 1/135* (2021.01); *C25B 9/09* (2021.01)

(58) Field of Classification Search
CPC .. H05H 1/461; H05H 1/42; A61L 2/14; B08B 7/0035; C25B 1/135; C25B 9/09; C25B 11/061; C25B 1/50; C25B 9/17; C25B 9/60; C25B 15/02; C25B 11/046; C25B 15/08; C25B 9/67; C01B 32/05; C01B 32/15; C01B 32/16; C01B 32/18; C01B 2202/06; C01B 2202/20; C01B 32/184; C01B 32/168; H01J 37/32192; B01J 19/088; B01J 19/126; B01J 2219/0894; B01J 2219/0879; B01J 2219/1281; B01J 23/745; B01J 2219/1296; B01J 2219/1227; B01J 2219/1215; B01J 2219/123; B01J 2219/1269; D01F 11/12; C01P 2006/42; B82Y 30/00; B82Y 40/00; B82Y 25/00; B82Y 35/00
See application file for complete search history.

(56) References Cited

U.S. PATENT DOCUMENTS

| | | | |
|---|---|---|---|
| 2011/0180385 A1* | 7/2011 | Imholt | B01J 19/126 |
| | | | 422/186.04 |
| 2020/0389967 A1* | 12/2020 | Lee | H05H 1/461 |
| 2021/0348282 A1* | 11/2021 | Licht | C25B 9/17 |

* cited by examiner

*Primary Examiner* — Xiuyu Tai
(74) *Attorney, Agent, or Firm* — Chamberlain, Hrdlicka, White, Williams & Aughtry; Aly Z. Dossa

(57) ABSTRACT

The embodiments of the present disclosure relate to a method and compounds for generating plasma. The method comprises exposing a carbon nanomaterial to a field of microwave radiation. Where the carbon nanomaterial is produced by molten carbonate electrolytic splitting of carbon dioxide.

16 Claims, 8 Drawing Sheets

METHOD FOR GENERATING MICROWAVE-DRIVEN PLASMA

TECHNICAL FIELD

This disclosure generally relates to a method of generating plasma. In particular, this disclosure relates to a method of generating plasma from carbon nanomaterials using fields of microwave radiation.

BACKGROUND

Cold and warm plasmas are non-thermal equilibrium plasmas, including not only free ions and electrons but also species which have not been fully ionized. While thermal (hot) plasmas maintain a high enough thermal energy to remain in the plasma state, non-thermal plasmas require an external power source to remain in the plasma state. While there are a number of practical uses for cold and warm plasmas, the current methods and apparatus for generating cold and warm plasmas can present technical difficulties and/or high costs. As such, new methods to generate such plasmas may be desirable.

Anthropogenic sources of carbon dioxide ($CO_2$) are known to contribute to the $CO_2$ collecting in our planet's atmosphere, as evidenced by the observed trend of atmospheric $CO_2$ levels increasing by about 50% in the last two hundred years. Increased levels of atmospheric $CO_2$ have been linked with increased temperatures around the world, with record-high temperatures recorded for more than 12 months in a row. Increased global temperatures are linked with increased frequency and intensity of destructive weather, increased frequency and intensities of heat-wave, decreased levels of glaciers and polar ice, and increased levels of seawater.

One approach for reducing atmospheric $CO_2$ levels is to use $CO_2$ and a carbonate electrolyte as participants in an electrolysis reaction for making graphene nanocarbon (GNC) structures. These electrolysis reactions may employ electrolysis potentials of less than 1 volt for splitting $CO_2$ in molten carbonate electrolyte to produce GNCs at high coulombic efficiency. The $CO_2$ taken from the atmosphere can be directly converted to GNCs, as confirmed by isotope ($^{13}C$) tracking. The electrolytic splitting of $CO_2$ in molten lithium-carbonate is efficient enough that it acts as a direct carbon capture method, and converts $CO_2$ from the air into GNCs without $CO_2$ pre-concentration, or the electrolysis process can be used with exhaust gas $CO_2$ or with concentrated $CO_2$.

GNCs are carbon nanomaterials with various shapes, referred to as allotropes, that retain the fundamental structure of graphene. GNCs have many useful properties including high physical-strength, high electrical-conductivity, high thermal-conductivity, electrical conductivity, high electron mobility, high stability, high aspect-ratio and a strong capacity to dissipate heat. The implication of these useful properties is that CNTs have had a steady rise in their applications. As but one example, adding low concentrations (typically much less than 1%) of GNCs into structural materials can increase the strength of a range of structural materials such as cement, steel, plastics, resins, and aluminum.

Another implication of the useful properties of GNCs is that a specific allotrope, carbon nanotubes (CNTs), are known to enhance electron field emissions at high voltages, high current and at higher efficiencies, as compared to thermal electron emitters, such as thermionic devices.

As such, it may be desirable to synthesize a GNC product from molten carbonate electrolytic splitting of $CO_2$ and employ the GNC product for various applications and uses.

SUMMARY

The embodiments of the present disclosure relate to a method for generating plasma. The method comprises the steps of generating a field of microwave radiation and exposing a carbon nanomaterial to the field of microwave radiation for generating the plasma.

In the embodiments of the present disclosure, the carbon nanomaterial may be a graphene nanocarbon (GNC).

In the embodiments of the present disclosure, the carbon nanomaterial may be graphene, a carbon nanotube (CNT), a carbon nanofiber (CNF), a thin-walled CNT, a carbon nanobamboo, a nano-pearl, a nano-tree, a conical CNF, a metal coated Ni-coated CNT, a nano-flower, a nano-dragon, a nano-rod, a nano-belt, a nano-onion, a hollow nano-onion (CNO), a nano-scaffold, a nano-platelet, and nano-helices.

Some embodiments of the present disclosure may relate to a step of providing the carbon nanomaterial as a product of an electrolysis process that splits carbon dioxide.

In the embodiments of the present disclosure, the method may further comprise a step of introducing a dopant to the electrolysis process for making a doped carbon nanomaterial.

In the embodiments of the present disclosure, the method may further comprise a step of introducing a magnetic additive component to the electrolysis process for making a magnetic carbon nanomaterial.

In the embodiments of the present disclosure, the method may further a step of directing the generated plasma at a a material for cleaning, purifying, disinfecting, healing, etching, modifying, toughening, polishing, promoting flow in, accelerating, decelerating, or activating the material, or any combination thereof.

In the embodiments of the present disclosure, the method may further a step of directing the generated plasma at a cell.

In the embodiments of the present disclosure, the method may further a step of directing the generated plasma for making a plasma shield or a heat shield, an electromagnetic shield, a drag shield or any combination thereof.

In the embodiments of the present disclosure, the method may further a step of directing the generated plasma for accelerating, trapping, and controlling a flow of ions or particles, or any combination thereof.

In the embodiments of the present disclosure, the method may further a step of directing the generated plasma for chemically reducing a gas.

In the embodiments of the present disclosure, the plasma may comprise excited carbon.

In the embodiments of the present disclosure, the plasma may comprise excited components of glass, borosilicate glass, alumina, sodium chloride, basalt, or any combination thereof.

In the embodiments of the present disclosure, the plasma may comprise excited sodium, excited chlorine, excited silicon, excited copper, excited cesium, or any combination thereof.

In the embodiments of the present disclosure, the plasma may comprise a gas.

In the embodiments of the present disclosure, the plasma may comprise a cold plasma, a warm plasma or any combination thereof.

In the embodiments of the present disclosure, the plasma may be energy efficient.

In the embodiments of the present disclosure, the plasma may be substantially free of any exotic species.

Without being bound by any particular theory, the plasma generated by exposing GNCs generated from the electrolytic splitting of $CO_2$ in a molten carbonate electrolyte may resemble the plasma generated by the observed plasmas a coaxial waveguide device, also referred to as a "microwave drill bit".

Herein it was observed generation of a plasma, triggered by exposing a GNC product to a field of microwave radiation-without a coaxial waveguide. In particular, multiwalled CNTs (MWCNTs) made from $CO_2$, appear to act as a channel of microwave energy, creating multiple hot spots, and directly inducing a plasma fireball without the need for a macroscopic device with a moveable antenna specifically placed within a coaxial waveguide. Without being bound by any particular theory, it may be that the physical chemical properties of MWCNTs as compared to single walled CNTs (SWCNTs)—contribute to this observed phenomena. Also, the specific physical chemical differences between a GNC product synthesized from molten carbonate electrolytic splitting of $CO_2$ and carbon nanotubes synthesized by other means, such as chemical vapor deposition (CVD) may contribute towards the plasma generated when the GNC product is exposed to a field of microwave radiation.

BRIEF DESCRIPTION OF THE DRAWINGS

These and other features of the present disclosure will become more apparent in the following detailed description in which reference is made to the appended drawings.

DETAILED DESCRIPTION

Figure 1:
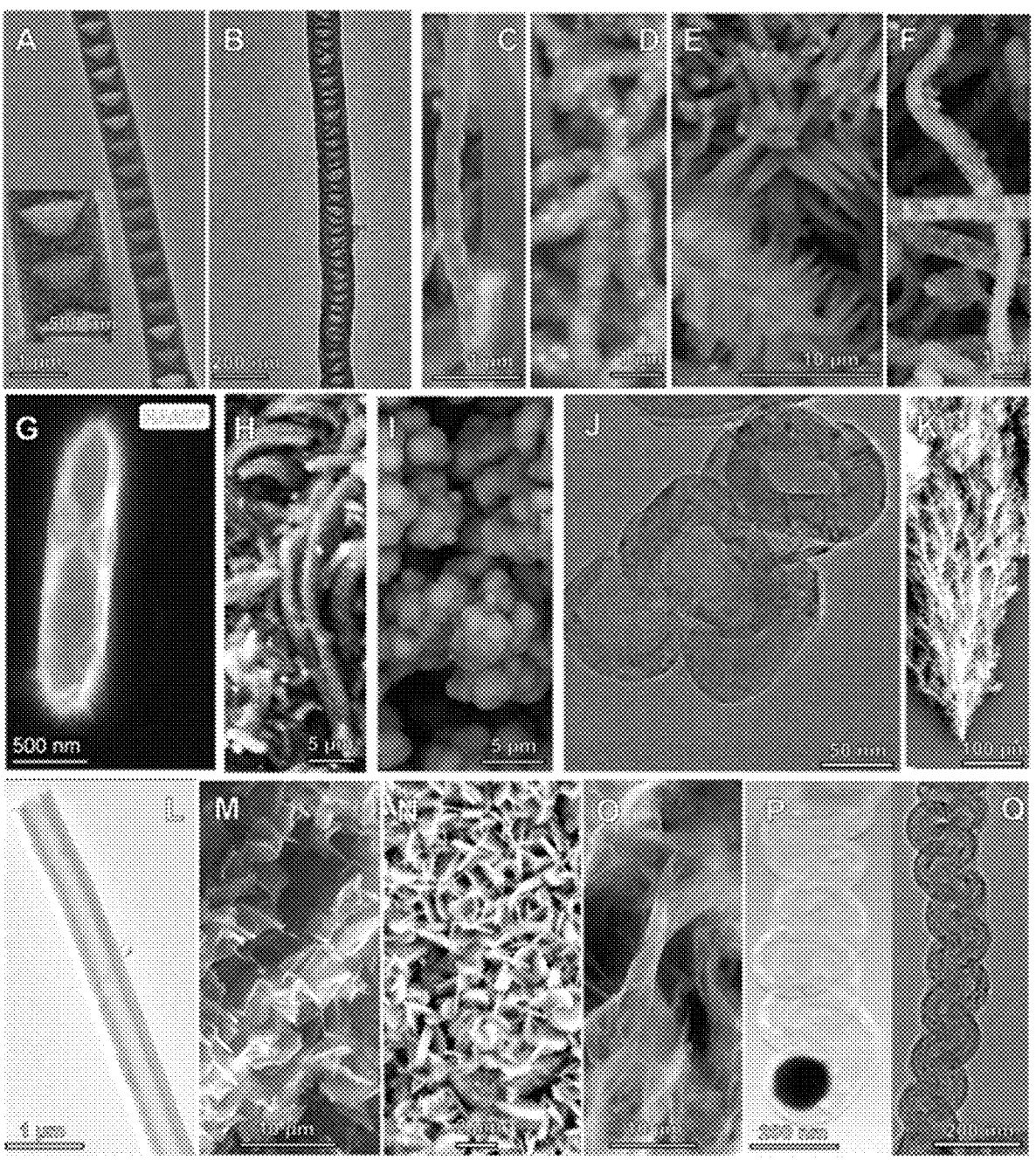
FIG. 1 shows a series of scanning electron microscope images of a variety of carbon nanostructure allotropes that can be produced by molten carbonate electrolytic splitting of carbon dioxide ($CO_2$).

The embodiments of the present disclosure relate to a method for generating plasma by exposing a graphene nanocarbon (GNC) product to a field of microwave radiation. Some embodiments of the present disclosure may also relate to methods and apparatus for producing a graphene nanocarbon (GNC) product that comprises graphitic carbon nanostructures, such as carbon nanotubes (CNTs), carbon nano-onions (CNOs), and other carbon nanostructures. The methods and apparatus employ carbon dioxide ($CO_2$) as a reactant in an electrolysis reaction in order to make the GNC product.

In some embodiments of the present disclosure, methods that employ an electrolysis reaction for making a GNC product may occur in an environment with a molten, carbonate electrolyte that is positioned between an anode and a cathode. Carbon is introduced into the molten electrolyte, as either pure $CO_2$, concentrated $CO_2$, $CO_2$ that is entrained in atmospheric air, as another carbon-containing gas, or other anthropogenic sources of $CO_2$.

The embodiments of the present disclosure also relate to a method for generating plasma by exposing the GNC product of the electrolytic splitting of $CO_2$ in a molten carbonate electrolyte to a field of microwave radiation.

Definitions

Unless defined otherwise, all technical and scientific terms used herein have the same meaning as commonly understood by one of ordinary skill in the art to which this disclosure belongs.

As used herein, the term "about" refers to an approximately +/–10% variation from a given value. It is to be understood that such a variation is always included in any given value provided herein, whether or not it is specifically referred to.

Embodiments of the present disclosure will now be described and include references to the Examples and the Figures.

Some embodiments of the present disclosure relate to a method for producing a GNC product that comprises CNTs. The method comprises the steps of heating a carbonate electrolyte to obtain a molten carbonate electrolyte; positioning the molten, carbonate electrolyte between an anode and a cathode in an electrolytic cell; applying an electrical current to the cathode and the anode in the electrolytic cell; and, collecting a GNC product from the cathode.

The GNC product is then exposed to a field of microwave radiation.

However, other embodiments of the present disclosure relate to other types of GNC containing products being exposed to a field of microwave radiation for generating plasma, where such GNC containing products are not the product of a molten carbonate electrolytic splitting of $CO_2$ process. Such GNC containing products may comprise GNC structures that have similar physical chemical properties as the GNC product made by the molten carbonate electrolytic splitting of $CO_2$, such as a greater number of walls, enhanced magnetic character of the GNC structures or other physical chemical properties that facilitate generating plasma when exposed to a field of microwave radiation.

The step of heating the carbonate electrolyte can be achieved by various approaches, as would be appreciated by the skilled reader. For example, a heating apparatus such as an oven or furnace can be used to heat the electrolyte to a sufficient temperature so that it transitions into a molten, liquid state. As such, any heating apparatuses that can achieve the temperatures required to heat the electrolyte to its melting point are contemplated herein.

In some embodiments of the present disclosure, the carbonate electrolyte may comprise lithium carbonate. For example, carbonates may include alkali carbonates and alkali earth carbonates. Alkali carbonates may include lithium, sodium, potassium, rubidium, cesium, or francium carbonates, or mixtures thereof. Alkali earth carbonates may include beryllium, magnesium, calcium, strontium, barium, or radium carbonates, or mixtures thereof. In some embodiments of the present disclosure, the electrolyte can be a mixed composition for example, a mix of alkali and alkali earth carbonates and one or more of an oxide, a borate, a sulfate, a nitrate, a chloride, a chlorate or a phosphate.

In some embodiments of the present disclosure, the carbonate electrolyte may be a low lithium carbonate. As used herein, the expression "low-lithium" means a low content of lithium such as when small amounts of lithium may be present, or when no detectable amounts of lithium are present. In some embodiments of the present disclosure, a "low-lithium carbonate electrolyte" is used to refer to a carbonate electrolyte that has less lithium present than a carbonate electrolyte that has lithium carbonate alone. For clarity, the expression "low-lithium carbonate electrolyte", is used here to refer to an electrolyte in which the lithium content is greater than about 5% on a weight basis (wt %) and less than about 100% wt % of the entire mixture. For clarity, the expressions "lithium-free carbonate electrolyte", and "predominantly non-lithium electrolyte" are used here in to refer to an electrolyte in which there is no detectable amount of lithium or where a small amount of lithium is present when the electrolyte is a mixture and the lithium-containing component forms less than about 5% wt % of the entire mixture or less than about 4 wt %, less than about 3 wt %, less than about 2 wt %, less than about 1 wt %, less than about 0.5 wt %, less than about 0.25 wt %, less than about 0.1 wt %, less than about 0.05 wt %, or less than about 0.025 wt % or less than about 0.01 wt % of the entire mixture.

The carbonate electrolyte can be a binary mixture, a ternary mixture, or a mixture of more than three components. For example, the binary mixture may comprise two components selected from: lithium carbonate, and either strontium carbonate, or strontium oxide, or any other strontium salt. A ternary mixture may comprise lithium carbonates, low-lithium carbonates or oxides, and a graphene-defect agent. A more complex mixture may include substances to dope the GNC product, enhance the thermal or electrical properties of electrolyte, or in other way modify the electrolyte or the GNC product.

Without being bound by any particular theory, the reduction of $CO_2$ in a lithiated or strontiated carbonate electrolyte is a $4e^-$ process that proceeds in accordance with Equation 1A or 1B (EQN. 1A or 1B):

$$Li_2CO_3(molten) + 4e^- \rightarrow \qquad \text{(EQN. 1A)}$$

$$C(nanomaterial;) + O_2(gas) + Li_2O(dissolved).$$

$$SrCO_3(molten) + 4e^- \rightarrow \qquad \text{(EQN. 1B)}$$

$$C(nanomaterial;) + O_2(gas) + SrO(dissolved).$$

Without being bound by any particular theory or idea, $CO_2$ added to the electrolyte chemically reacts with lithium oxide to renew and reform $Li_2CO_3$ in accordance with Equation 2A or 2B (EQN. 2A or 2B):

$$CO_2(atmospheric\ or\ stack) + Li_2O(dissolved) \rightleftharpoons \qquad \text{(EQN. 2A)}$$

$$Li_2CO_3(molten).$$

$$CO_2(atmospheric\ or\ stack) + SrO(dissolved) \rightleftharpoons SrCO_3(molten). \quad \text{(EQN. 2B)}$$

Without being bound by any particular theory, when EQN. 1A or 1B is combined with EQN. 2A or 2B yields a net electrolysis reaction, in accordance with Equation 3 (EQN. 3):

$$CO_2(gas) + 4e^- \rightarrow C(nanomaterial) + O_2(gas). \qquad \text{(EQN. 3)}$$

Without being bound by any particular theory, at temperatures higher than about 800° C., a two, rather four, electron reduction can increasingly dominate, and by about 950° C., the electrolysis product is pure carbon monoxide (CO), rather than carbon, in accordance with Equation 4 (EQN. 4):

$$CO_2(gas) + 2e^- \rightarrow CO(gas) + 1/2O_2(gas). \qquad \text{(EQN. 4)}$$

Without being bound by any particular theory, the embodiments of the present disclosure relate to electrolytes that facilitate GNC formation including: (i) low-lithium agents that include non-lithium salts including, but not limited to: strontium carbonate, beryllium carbonate, sodium carbonate, calcium carbonate, barium carbonate and oxides, such as strontium oxide, barium oxide, beryllium oxide, sodium oxide, calcium oxide, iron oxide, cobalt oxide, lithium oxide or any combination thereof (to allow carbon nanomaterials to form); (ii) molten and stable between about 700° C. and about 850° C.; (iii) able to readily dissolve oxides; and, (iv) inexpensive as compared to lithium carbonate. Strontium carbonate has a high melting point of about 1494° C. Strontium carbonate and strontium salts are an order of magnitude less expensive than lithium carbonate.

The molten electrolyte is then positioned between an anode and a cathode within an electrolytic cell. The electrolytic cell may be any type of vessel that can maintain its structural integrity in the face of the electrochemical environment that occurs during the electrolysis reactions of the present disclosure. The electrolytic cell may have one or more walls that may be made of a desired material or that are coated with a desired material that will not degrade in the environment of the electrolysis reaction. In some embodiments of the present disclosure, the electrolytic cell is made of substantially pure alumina; in other embodiments the electrolytic cell is made substantially of a corrosion resistant metal, including but not limited to, stainless steel, inconels, and other nickel containing alloys. In some embodiments of the present disclosure, the electrolytic cell is a tubular vessel with a closed end. Other embodiments include, but are not limited to square, rectangular or other shaped vessels to contain a molten electrolyte.

In some embodiments of the present disclosure, the electrolyte mixture may be melted inside the electrolytic cell or it may be melted outside the cell and transferred thereto. Because the electrolysis reaction will typically occur over a time period whereby the molten electrolyte could cool, the electrolytic cell can be configured with its own integral heating apparatus, such as an integral heater or other apparatus that may be self-heating through ohmic resistance and exothermic reactions, or it may be configured to be heated by an external heater that is external to the electrolytic cell so that the electrolyte is maintained in the molten state for the desired period of time.

In some embodiments of the present disclosure, the electrolytic cell maybe configured to maintain the electrolyte at less than about 400° C., at least at about 400° C., at least at about 500° C., at least at about 600° C., at least at about 625° C., about 650° C., at least at about 675° C., at least at about 700° C., at least at about 725° C., at least at about 750° C., at least at about 775° C., at least at about 800° C., at least at about 825° C., at least at about 850° C., at least at about 875° C., at least at about 900° C., at least at about 1000° C. or greater than about 1000° C.

The anode can be made of various metals or alloys. Some anodes can be made of materials that comprise nickel. Some non-limiting examples of suitable materials for the anodes of the present disclosure include: substantially pure nickel, an alloy that is comprised of substantially mostly nickel, an alloy that is comprised of some nickel. For example, stain-less steel 304 or stainless steel 306 or other stainless steels, Inconel 718 or other Inconels, such as, but not limited o Inconel 600 and Inconel 625, Nichrome A (composed of about 80% nickel and about 20% chromium), Nichrome C (composed of nickel, iron and chromium), Incoloy alloy (such as Incoloy 800 composed of about 40% iron, about 30-35% nickel and about 19-23% chromium).

The anode may be planar in shape and it can be made of various dimensions. In some embodiments the cathode may be of any geometric shape. The cathode may be smooth or roughened. The cathode may have an area of less than 1 cm₂, or between 1 and 100 cm$^2$, or between 100 and 10,000 cm$^2$, or larger. In some embodiments of the present disclosure, the anode may be made of wire that is rolled into a substantially flat coil with an upper face and a lower face. The upper and lower faces of the coiled anode may have substantially equal areas that are suitable for fitting within the electrolytic cell. In some embodiments, the coiled anode faces have an area that is between about 1 cm$^2$ and about 20 cm$^2$; between about 2 cm$^2$ and 10 cm$^2$; or between about 3 cm$^2$ and about 5 cm$^2$. The skilled person will appreciate that the size of the electrolytic cell may dictate the size of the coiled anode. The coiled anode may be arranged to be generally aligned with a horizontal plane, with a vertical plane or therebetween. In some embodiments of the present disclosure, the walls of the electrolytic cell may be made of or lined with a material that acts as an anode.

The cathode can be made of various metals or alloys. Some cathodes can be made of materials that comprise steel, galvanized steel, copper, or any combinations thereof. Some further non-limiting examples of suitable materials for the cathodes of the present disclosure include: copper alloys such as Monel, $Cu_2O_2$, Cu708, bronzes, brasses, such as Muntz Brass, or a combination thereof.

The cathode may be planar in shape and can be made of various dimensions. In some embodiments the cathode may be of any geometric shape. The cathode may be smooth or roughened. The cathode may have an area of less than 1 cm$^2$, or between 1 and 100 cm$^2$, or between 100 and 10,000 cm$^2$, or larger. In some embodiments of the present disclosure, the cathode may be made of wire that is rolled into a flat coil with an upper face and a lower face. The upper and lower faces of the coiled cathode may have substantially equal areas that are suitable for fitting within the electrolytic cell. In some embodiments, the coiled cathode faces have an area that is between about 1 cm$^2$ and about 20 cm$^2$; between about 2 cm$^2$ and 10 cm$^2$; or between about 3 cm$^2$ and about 5 cm$^2$. The skilled person will appreciate that the size of the electrolytic cell may dictate the size of the coiled cathode. The coiled cathode may be arranged to be generally aligned with a horizontal plane, with a vertical plane or therebe-tween.

In some embodiments of the present disclosure, the size and orientation of the cathode can be selected to substan-tially mirror the size and orientation of the anode. In some embodiments of the present disclosure, the anode and the cathode may be generally aligned with a horizontal plane and vertically spaced apart from each other. As the skilled person will appreciate, the distance between the electrodes must permit the passage of sufficient electric current ther-ebetween but the amperage of the electric current and the size of the electrolytic cell may also influence how far apart the electrodes are vertically spaced apart. In some embodi-ments of the present disclosure, the electrodes may be vertically spaced apart from each other by about 0.25 cm, about 0.5 cm, about. 0.75 cm, about 1 cm, about 1.25 cm, about 1.5 cm, about 1.75 cm, about 2 cm, about 3 cm, about 4 cm, about 5 cm, about 7.5 cm, about 10 cm or further.

In order to initiate and maintain the electrolysis reaction within the electrolytic cell, an electric current is supplied from a source of electric current and while the current is applied, it passes between the anode and cathode via the molten electrolyte therebetween. In some embodiments of the present disclosure, the electric current may be an alter-nating current or a direct current. In some embodiments of the present disclosure, the current may be between about 0.01 amps (A) and about 5 A. In some embodiments of the present disclosure, the current may be between about 0.025 A and about 4 A; between about 0.05 A and about 3 A; between about 0.075 A and about 2 A; between about 0.1 A and about 1 A. In some embodiments of the present disclo-sure the current is about 0.5 A.

In some embodiments of the present disclosure, the cur-rent is applied at a substantially constant current density. For example, the current density of the applied current may be between about 0.001 A/cm$^2$ and about 10 A/cm$^2$. In some embodiments of the present disclosure, the current density of the applied current may be between about 0.02 A/cm$^2$ and about 0.2 A/cm$^2$; between about 0.05 A/cm$^2$ and about 1.0 A/cm$^2$; between about 0.075 A/cm$^2$ and about 0.75 A/cm$^2$; or between about 0.01A/cm$^2$ and about 0.1 A/cm$^2$. In some embodiments of the present disclosure, the current density is about 0.1 A/cm$^2$. In some embodiments of the present disclosure, an initial lower current density is used to control conductivity during the formation of the GNC product and a second higher current density is used to facilitate growth of the GNC product.

In some embodiments of the present disclosure, the method further comprises the step of employing one or more GNC facilitation elements within the electrolysis reaction. In some embodiments of the present disclosure, the one or more non-lithium GNC facilitation elements may comprise: (i) adding a non-lithium salt, such as but not limited to: a strontium salt, a beryllium salt, a sodium salt, a calcium salt, a barium salt, a radium salt, (ii) adding a transition metal nucleating agent to enhance transition metal nucleation, iii) adding one or more defect inducing agents, (iv) reducing or removing an electrolyte conductivity impediment element, and (v) any combination thereof.

In some embodiments of the present disclosure, the step of enhancing transition metal nucleation may comprise adding a transition metal nucleating agent to the electrolyte, either before, during or after the heating step. In the process of a $CO_2$ molten carbonate electrolysis reaction, small tran-sition metal "seeds" have been observed at the ends of CNT structures within the GNC product. It has been shown that the mechanism of molten carbonate GNC growth may be activated by both tip and root transition metal nucleation processes by the use of transition metals as nucleating agents. In some embodiments, the transition metal nucleat-ing agent may be a transition metal salt of one or more of an iron, chromium, nickel, copper, manganese, titanium, zirco-nium, molybdenum, tantalum, tungsten, silver, cadmium, tin, ruthenium, vanadium, or cobalt salt. In some embodiments, the transition metal nucleating agent may be a transition metal oxide, such as nickel oxide, iron oxide, chromium oxide, or a combination thereof. For clarity, the amount of transition metal nucleating agent added may result in a small amount of the transition metal being incorporated into a portion of the one or more individual nanostructures within the GNC product. However, the transition metal nucleating agent is not incorporated into the individual nanostructures to such an extent so as to dope the GNC product. As discussed further below, a doped GNC product has different physical-chemical properties than a GNC product made with the assistance of a transition metal nucleating agent. Without being bound by any particular theory, the doped GNC product may have atoms of a dopant incorporated throughout the entirety of each individual nanostructure and it is that more wholesome incorporation of dopant atoms that imparts the different physical-chemical properties of a doped GNC product as compared to a non-doped GNC product.

In some embodiments of the present disclosure, the step of adding one or more defect inducing agents comprises a step of introducing a graphene-defect agent into the carbonate electrolyte, either before, during or after the heating step. This adding step can be achieved by various approaches, depending on what the nature of the graphene-defect agent is. For example, the graphene-defect agent may be a chemical, a mechanical element, an optical element, a physical element, or any combination thereof that induces graphene defects and/or graphene vacancies in graphitic structures of the GNC product.

In some embodiments of the present disclosure, the graphene defects are localized within a graphene component of the graphitic carbon nanostructures within the GNC product and the defects are intrinsic, extrinsic, or any combination thereof.

Examples of intrinsic graphene defects are Stone-Wales defects, single vacancy defects, multiple vacancy defects, line defects, the inclusion of carbon adatoms, or any combination thereof.

Examples of extrinsic graphene-defects are the inclusion of foreign adatoms or substitutional impurities.

In adatom defects, oxygen may attach to the surface of the CNT or other carbon nanomaterials and disrupt the bonding, or may replace carbon in the structure itself.

In some embodiments of the present disclosure, the graphene-defect agent is an oxide. The oxide may be introduced into the carbonate electrolyte by adding a chemical oxide, by a chemical reaction caused by a change in the temperature of the molten carbonate electrolyte, by degradation of the electrodes, by oxidation of the anode or any combination thereof.

Suitable examples of chemical oxides that may be added into the carbonate electrolyte include, but are not limited to: an alkali oxide, an alkali earth oxide, a metal oxide, a non-metal oxide or any combination thereof. In some embodiments of the present disclosure, one or more oxides may be added to the low-carbonate electrolyte, including but not limited to: strontium oxide (SrO), sodium oxide ($Na_2O$), barium oxide (BaO), beryllium oxide (BeO), calcium oxide (CaO), aluminum oxide ($Al_2O_3$), or any combination thereof. Combinations may also be added as reorganized oxide salts, for example, without being limited to, sodium or barium aluminate. In some embodiments of the present disclosure, the oxide is one or more of barium oxide, sodium oxide or calcium oxide. In some embodiments of the present disclosure, the oxide is iron or cobalt oxide. In some embodiments of the present disclosure, the oxide is lithium oxide at a concentration of about 5 percent by weight (wt %) or less.

Without being bound by any particular theory, the carbonate species, generated from the continuous $CO_2$ renewal of the low-lithium carbonate electrolyte provide the ongoing carbon building blocks of the nanostructures within the GNC product, and the carbonate reduction to carbon may or may not occur at a metal catalyst interface with the growing nanostructure, such as the graphene walls of a CNT. However, carbonate must have easy access not only to the interface with the outer CNT walls, but also to interface with the inner CNT walls. Carbonate movement to the interior of the growing carbon nanotube may be inhibited by charge buildup. This charge buildup may be reduced if cations also have easy access to the interior walls. The lithium cation is a small cation, and requires relatively few defects or vacancies in the growing cylindrical carbon nanotube walls to access the interior regions of the CNT. However, a higher number of defects is required to facilitate ions larger than lithium cations to transfer through the CNT walls. A higher number of defects may be accomplished through the addition of a graphene-defect agent. This is, at least part of, the basis upon which the embodiments of the present disclosure were developed to grow a GNC product by $CO_2$ electrolysis in low-lithium carbonate electrolyte.

The use of an electrolyte that is a binary mixture (for example, strontium carbonate/lithium carbonate or strontium oxide/lithium carbonate), and/or an electrolyte that is a ternary mixture (for example, strontium/sodium/lithium carbonate), and/or has more components and that can provide an electrolyte melting point within the optimal range for $CO_2$ to carbon nanomaterial growth of between about 700° C. to about 850° C. Low-lithium electrolysis may be performed using a planar, rather than a coiled, and brass, rather than Monel, cathode without substantially affecting low-lithium CNT growth.

Because strontium carbonate and strontium oxide are substantially less expensive than comparable lithium-carbonate based electrolytes and because strontium is widely available, strontium salts are suitable candidates for making a low-lithium carbonate salt. However, strontium carbonate ($SrCO_3$) is solid at 1494° C., which is too high for $CO_2$ electrolysis to synthesize solid GNC products. The inventors have demonstrated that temperatures below 800° C. are suitable for $CO_2$ molten carbonate electrolysis. At higher temperatures, carbon monoxide gas increasingly forms, and the product is pure carbon monoxide gas by 950° C. Carbon monoxide is not preferred as a decomposition product because its main use is as an oxidant, and in that use the carbon monoxide returns $CO_2$ to the atmosphere. Alternatively, GNCs retain the high (geologic stability) of the mineral graphite to sequester the $CO_2$ reactant.

In some embodiments of the present disclosure, the GNC product made according to the methods, apparatus and systems described herein above, may result in a doped GNC product. Without being bound by any particular theory, if a doping component, also referred to as a dopant, is introduced into the method, apparatus or system, then atoms of the dopant may be directly incorporated into various of the graphitic structures of the GNC product. When atoms of the doping component are directly introduced into the GNC product, as it is being built in situ upon the cathode, the resulting doped GNC product has desired chemical physical properties that are different than a GNC product (a non-doped GNC product) that does not include atoms of the doping component. Without being bound by any particular theory, the doping component may include at least one material with a group IIIA element, a non-carbon group IVA element, a group VA element, a group VIA chalcogenide element, or at least one material with gold, platinum, iridium, iron or other row 4, 5, or 6 metals. In some embodiments of the present disclosure, the doping component comprises: a chemical species with oxygen atoms, halide atoms, one or more of nitrate, a phosphate, a thiophosphate, a silicate, a thionyl chloride, a sulfur chloride, a silicon chloride, a thiophosphate, a thionyl nitrate, a silicon nitrate, a silicon nitrite, a sulfur oxide and a nitrous oxide gas. Without being bound by any particular theory, the desired chemical properties of the doped GNC product may include: a greater electrical conductivity (as compared to a non-doped GNC product), enhanced electrical charge storage (as compared to a non-doped GNC product), a heterogeneous catalytic property, a homogeneous catalytic property, a fuel cell catalytic property, an aerobic oxidation catalytic property, an enhanced reaction activity property and any combination thereof. The desired physical chemical properties of the doped GNC product made according to the embodiments of the present disclosure may have a wide variety of applications, such as: catalysts, heavy metal removal, energy storage, sorption applications, batteries, ultra-sensitive sensors and combinations thereof. For clarity, transition metals that are used as a nucleating agent during the initial root or tip growth phase of making the carbon nanostructures constituent within the GNC product are either not the type of chemical element that will impart the desired chemical properties to the constituent structures of the GNC product or they are not used in a sufficient amount so as to impart the desired chemical properties.

In some embodiments of the present disclosure, the GNC product made according to the methods and apparatus described herein above, may result in a magnetic GNC product. For clarity, a magnetic GNC product is includes magnetic carbon nanostructures as constituent structures where some, most or substantially all of such constituent carbon nanostructures contain a sufficient amount of magnetic chemical elements so as to be physically movable with a magnetic field. For example, the movability in response to a magnetic field may be due to the increased presence of magnetic chemical elements positioned within individual carbon nanostructures that are constituent within the GNC product, where such presence extends substantially throughout each carbon nanostructure. This substantial extension throughout each carbon nanostructure is in contrast with the presence of nucleation agents, such as a transition metal, that facilitates the initial root or tip growth of a given carbon nanostructure within the GNC product. For clarity, transition metal nucleating agents may be useful in contributing towards making magnetic carbon nanostructures but such nucleating agents alone are insufficient in making magnetic carbon nanostructures as they do not impart a sufficient amount of magnetic chemical elements into the carbon nanostructures. Without being bound by any particular theory, if a magnetic additive component, is introduced into the method, apparatus or system, then growth of various carbon nanostructures within the magnetic GNC product occurs. In some embodiments of the present disclosure, the magnetic additive component comprises at least one of a magnetic material addition component, a carbide-growth component and any combination thereof. In some embodiments of the present disclosure, the magnetic material addition component is wherein the magnetic material additive component is one or more of iron, nickel, cobalt, gadolinium, samarium, neodymium, steel and alloys comprising one or more magnetic materials with ferromagnetic properties, paramagnetic properties, diamagnetic properties and any combination thereof. In some embodiments of the present disclosure, the iron-based additive is one or more of cast iron powder, iron metal, steel, stainless steel, an iron containing metal alloy, an iron oxide, $FeO$, $Fe_2O_3$, $Fe_3O_4$, or an iron-containing salt. Within the magnetic GNC product, the magnetic additive component is incorporated or formed as one or more nodules that may be covered in one or more layers of graphitic carbon, on the magnetic GNC product. In some embodiments of the present disclosure, the carbide-growth component may be a metal carbide, such as: iron carbide, a nickel carbide, a cobalt carbide; a zirconium carbide, a chromium carbide, a tantalum carbide, a hafnium carbide, and any combination thereof. In some embodiments of the present disclosure, the carbide-growth component may be a non-metal carbide, such as silicon carbide, a germanium carbide, and any combination thereof. The magnetic additive component may be added to the methods, apparatus and systems of the present disclosure, as a chemical additive or it may originate from one or more walls of the electrolysis cell, from the anode, from the cathode, the electrolyte media, and any combination thereof.

The embodiments of the present disclosure relate to methods for generating plasma by exposing the GNC product—as synthesized by the electrolysis methods and apparatus described herein above that utilize $CO_2$ as a reactant—to a field of microwave radiation. As referenced herein, the term "plasma" refers to a superheated gas that may comprise both positively charged ions and negatively charged ions in a combination of ions and electrons. The plasma generated according to the embodiments of the present disclosure may be used in numerous applications such as altering the surface of another material to activate the surface of the other material, cleaning surfaces, coating a surface, cutting through materials, cauterizing and cleaning wounds and other applications understood by those skilled in the art.

Graphite surfaces and powders have been modified with various applied plasmas; surface effects are known to be more pronounced under argon plasmas. While microwaves have been used to selectively heat natural graphites, and microwaves are known to induce localized heating and purification in graphites.

Microwaves or (non-plasma) pyrolysis have been used to modify GNCs and specifically CNTs. Microwave-driven plasmas have been generated in gases including He, Ar, $N_2$, $O_2$, $CO_2$, and air. Microwave-driven gas plasmas have been used to synthesize, treat, or modify CNTs and graphene. GNCs have also been synthesized or treated with gas plasmas generated by means other than microwaves, such as inductively coupled plasma arcs, and/or plasma torches. However, none of these prior interactions between plasma and GNC use any form of GNCs to generate (trigger and sustain) microwave-driven plasmas as provided for by the embodiments of the present disclosure.

CNT and GNC physical-chemical characteristics may facilitate a prospective microwave-driven plasma formation. CNTs and carbon nano-onions (CNOs) exhibit high microwave absorptivity. CNTs have high strength, electrical conductivity, electron mobility, stability, high aspect ratio and a strong capacity to dissipate heat. CNTs enhance electron field emissions; such properties may also be conducive to potential microwave-driven plasmas. Emitting and focusing electrons at high voltages can induce gas and particle ionization at lower temperatures than expected by purely thermal means. CNTs have been shown to emit electrons at high voltages, currents, and efficiency compared to thermal electron emitters of electrons such as thermionic devices.

During electrolysis, $CO_2$ is split into $O_2$ and GNCs. These GNCs are a matrix of interconnected structures with the electrolyte on the cathode, as illustrated in FIG. 12. Synthesized GNCs also encompass helical, thin-walled, magnetic, and doped CNTs, along with carbon nano-bamboo, nano-pearl, nano-tree morphologies, and graphene. Additional specifics regarding the electrolysis process, including product separation from excess electrolyte and product washing, have recently been documented. This mixture of GNCs and carbonate electrolyte at the cathode is termed a carbanogel. The carbanogel is purified by separating the GNCs from the electrolyte. $CO_2$ electrolysis parameters are manipulated to tailor the type of GNC produced by controlling the temperature, current density, and electrolyte composition. For instance, a lower temperature (725 C) is typically used for the $CO_2$ electrolytic production of CNOs, while a higher temperature range (750-770° C.) is employed for synthesizing CNTs through electrolysis.

Control of the electrode and electrolyte composition, and $CO_2$ electrolysis splitting temperature and current density tunes the decarbonization process to form a range of specific GNC generated by control of the temperature, current density, and the composition of the electrolyte [8]. For example, a lower temperature (725° C.) is typically used in the electrolytic growth of carbon nano-onions, while higher temperature (750 to 770° C.) is used in the electrolytic growth of carbon nanotubes. Lithium carbonate, a typical electrolyte, has a melting point of 723° C. Binary lithium carbonate mixtures have a lower melting point. A high sodium carbonate content in a mixed sodium/lithium carbonate electrolyte and a lower electrolysis temperature (670° C.) drive the formation of a graphene scaffold nanocarbon product formation. Applied electrolysis current densities generally range from 0.03 to 0.6 A $cm^{-2}$. High current density (0.6 A $cm^{-2}$ or over) is one of the principal conditions driving the formation of helical, rather than straight, carbon nanotubes.

Electrode (and electrolyte additive) composition variation has been used to grow a number of other GNC allotropes from $CO_2$. These include carbon nanobamboo, carbon nanopearl, graphene from nanocarbon platelets, carbon nanofiber, carbon nanobelt, carbon nanotree, and other specific carbon allotrope morphologies. FIG. 1 shows scanning electron microscope (SEM) images of a range of these GNC products. SEM of nanocarbon allotropes synthesized by the electrolytic splitting of CO2 in molten carbonate. In FIG. 1 the top row (from A to F) of images shows: conical CNF (panel A), nano-bamboo (panel B), nano-pearl (panel C), Ni coated CNT (panel D), nano-flower (panel E), and nano-dragons (panel F). The middle row of FIG. 1 shows (from G to K) images of: nano-rod (panel G), nano-belt (panel H), nano-onion (panel I), hollow nano-onion (panel J), and nano-trees (panel K). The bottom row of FIG. 1 (from L to Q) shows: carbon nanotube (panel L), nano-scaffold (panel M), nano-platelet (panel N), graphene (panel O), and nano-helices (panels P and Q). The operational parameters for synthesizing these GNC allotropes are described in X. Liu, G. Licht, X. Wang, S. Licht, Controlled Growth of Unusual Nanocarbon Allotropes by Molten Electrolysis of $CO_2$ (Catalysts 12 (2022) 137. https://doi.org/10.3390/catal12020125) the contents of which are incorporated herein by reference.

The direct conversion of $CO_2$ to a GNC product provides an opportunity to remove this greenhouse gas while producing these stable GNC allotropes, thereby contributing to climate change mitigation. Long-term $CO_2$ removal is a critical component of effective carbon capture. Graphite, a macroscopic form of layered graphene, serves as a mineral with a geological lifespan spanning hundreds of millions of years, offering a stability benchmark for synthesized graphene nanocarbon materials.

The embodiments of the present disclosure relate to exposing the GNC product to a field of microwave radiation. As will be appreciated by those skilled in the art, microwave radiation can be generated by various methods and apparatus, such as vacuum tubes and an electric field and/or a magnetic field, field-effect transistors and the like. While the embodiments and examples described herein relate to microwave ovens, all other methods and apparatus for generating electromagnetic radiation in wavelengths longer than infrared waves and shorter than radio waves are contemplated herein.

Without being bound by any particular theory, the embodiments of the present disclosure provide an intense GNC self-induced, continuous microwave plasma that is spatially confined, but produced in an open container. In one embodiment the GNC is a CNT. In one case of that embodiment, the sole reactant preparing these CNTs is $CO_2$. Such continuous plasmas have not yet been not found to be induced by other GCNs prepared by conventional methodologies. However, without being bound by any theory, GCNs, such as CNTs, prepared by other methodologies to include physical chemical properties that make the GCNs made by molten carbonate electrolytic splitting of $CO_2$ suitable for generating plasma by exposure to a field of microwave radiation may also be suitable for generating plasma when exposed to a field of microwave radiation. Examples of such physical chemical properties include, but are not limited, to an increased number of graphene walls and/or an enhanced magnetic character of the GCNs may also impart the capability to generate sustained microwave-driven plasmas. Furthermore, the plasma may be effective in purifying the GNC product of impurities, such as electrolyte or otherwise.

EXAMPLES

Figure 2:
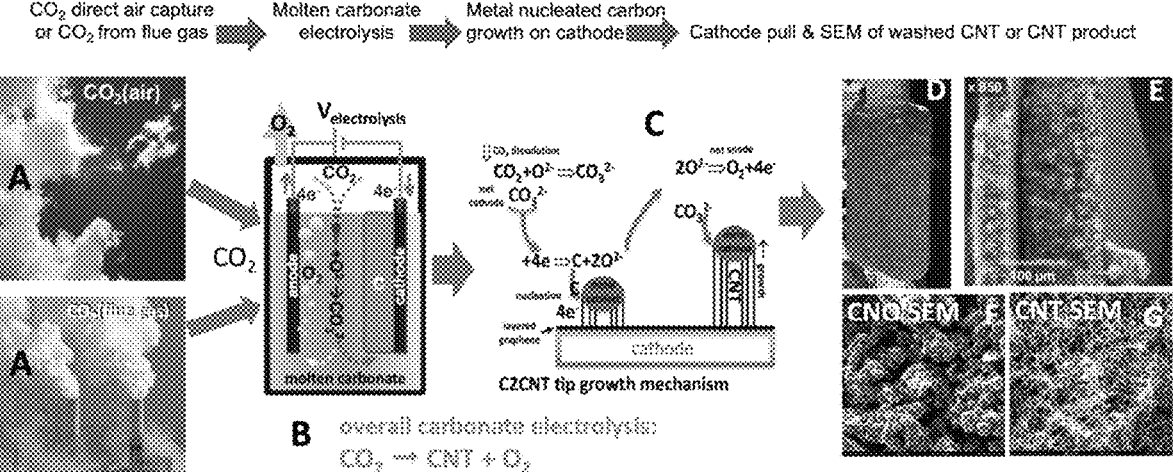
FIG. 2 is a schematic that represents a high-level overview of a molten carbonate electrolytic process for splitting of carbon dioxide $CO_2$ for producing a graphene nanocarbon (GNC) product.

FIG. 2 provides an overall schematic of electrolysis process for splitting $CO_2$ to synthesize a GNC product. In FIG. 2, panel A: $CO_2$ is removed directly from air or flue gas (without preconcentration), panel B depicts $CO_2$ electrolyzed in the molten carbonate electrolyte. Panel C shows transition metal nucleated mechanism of electrolytic $CO_2$ transformation into a GNC product, in this case CNTs are formed at the electrolysis cathode. Panel D shows a 1700 $cm^2$ cathode with carbanogel thereupon. The carbanogel comprises CNTs with interstitial electrolyte, the carbanogel was formed subsequent to an 18-hour electrolysis at 0.6 A/$cm^2$ in 770° C. $Li_2CO_3$. Panel E shows an SEM image of the carbanogel subsequent to excess electrolyte removal (100 μm scale bar), panel F shows SEM images of carbon nano-onions and panel G shows CNTs within the GNC electrolysis product (10 μm scale bar).

Carbanogel Formation From $CO_2$

Lithium carbonate was purchased at a battery grade >99.5% and was used as received. As analyzed, the lithium carbonate had a composition of 99.8% ($Li_2CO_3$, Green Chemical Co.). HCl, (31.45% Cleartech) $H_2O_2$ (35%, Aquabond), $HNO_3$ (70% ACS reagent, Sigma) and $HClO_4$ (70% ACS reagent, Sigma) were used in GNC purification. Muntz brass is a high-zinc brass alloy composed of 60% copper and 40% zinc by weight; and also referred to as 280 brass. This material served as the cathode and was purchased from onlinemetals.com and in larger quantities from Marmetal Industries. Electrolysis was conducted in 304 stainless steel "carbon pots". The pot acts as both the cell case and its inner walls served as the anode.

$CO_2$ was split in molten $Li_2CO_3$ between a Muntz brass cathode and a 304 stainless steel anode. The $CO_2$ source of the CNTs was flue gas from the Shepard Energy Centre natural gas power plant in Calgary, CA with about 5% $CO_2$ content. Nanocarbon on the cathode grows as a carbanogel matrix with interstitial electrolyte as in the SEM in FIG. 2E. A benefit of isolating nanoparticles within a macroscopically sized matrix as agglutinated, particles is that these macroscopic carbanogel particles mitigate respiratory hazards. Specifically, potential hazards sometimes associated with shipping nanoscopic particles are avoided. Other benefits are the structure provides an electrically and thermally conductive matrix, along with a highly porous framework for the accommodation of composite materials, and catalytic sites, or battery intercalation. The SEM of the GNC carbanogel shown in FIG. 2, panel E is of a CNT product after an initial HCl wash to out impurities. At higher SEM magnification such as shown in FIG. 2, panel G, the same electrolysis product shows that the individual carbanogel particles are composed of high-purity CNTs. Other electrolysis conditions such as lowering of the electrolysis temperature led to the formation of CNOs, as shown in FIG. 2, panel F.

TGA and Microscopy of the Carbanogel Product

Thermogravimetric analysis (TGA) of the product was analyzed with a Perkin Elmer STA 6000 TGA/DSC. E. SEM images were obtained performed using a PHENOM Pro-X scanning electron microscope. TGA is conducted under air, from 30-800° C. at 5° C./min. Measured TGA % residue multiplied by ⅔ approximately compensates for residual mass added during oxidation, and subtracted from 100% is a TGA estimate of purity. The inflection point temperature, $T_{infl}$, at the peak of the derivative of the TGA mass change provides measure of a material's oxidation resistance.

CNT-Induced Microwave Plasma Generation

Subsequent to $CO_2$ electrolysis, a desired weight of the washed, ground carbanogel was placed in borosilicate (Pyrex) Erlenmeyer flasks, beakers, or (alumina) ceramic crucibles. The sample was then placed at the center of a microwave oven for 1 minute, the sample was filmed while the microwave field was applied, and the heating, electrical, and plasma quality of the product was observed. Two different microwave ovens were employed. One was a conventional (Toshiba 201) 650 W output power laboratory microwave with a turntable and a 16 L chamber volume. The turntable homogenizes the applied microwave field, avoiding extended exposure to low or high variations in the microwave field. The second was a commercial-scale Panasonic NE-3280 microwave, with 3200 W output power, a ceramic floor, and no visible turntable. The NE-3280 provides a larger 44 L microwave chamber, a 5-fold higher microwave power, and internal turntables below the ceramic floor and in the microwave ceiling to apply the microwave field homogeneously.

For comparison, tested CNTs were alternatively treated with a conventional RF-driven plasma using a TCH-55, generating 300 W of RF plasma. The TCH-5S is driven by a 40 KHz RF frequency and has a 150 mm×270 mm inner chamber with a 5 L capacity. All plasmas were generated in ambient air.

CNT Self-Purification by the Induced Microwave Plasma

Plasmas were applied to various CNT samples and were characterized by TGA. Self-induced microwave or RF plasmas were applied to the samples for a fixed duration, and post-treatment were then again characterized by TGA.

Figure 3:
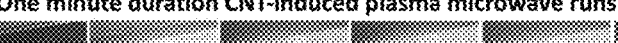
FIG. 3 is a series of photographic images that show a plasma product of exposing a GNC product to a field of microwave radiation.
Figure 3:
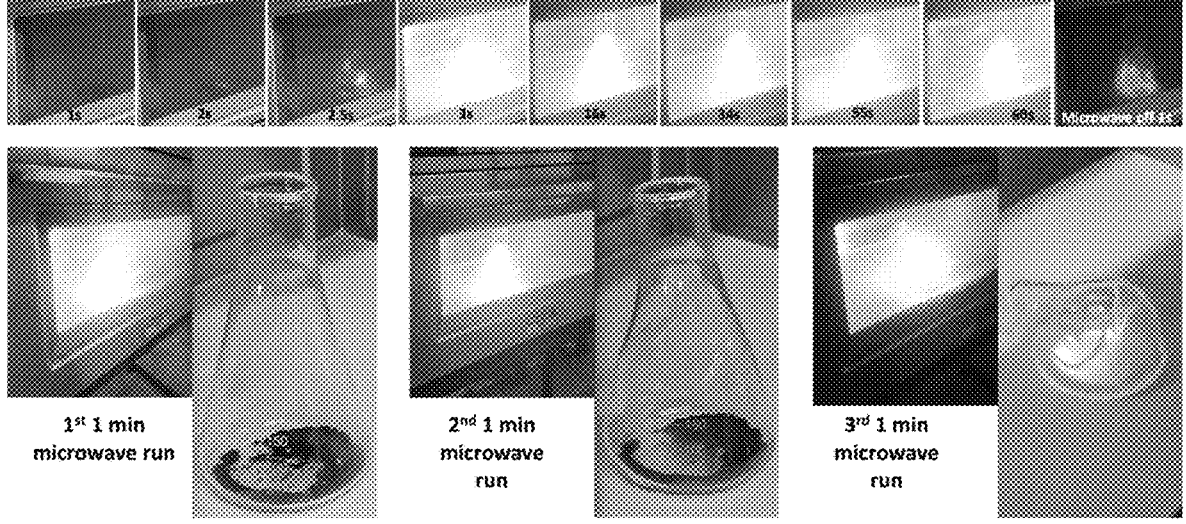

Observation of Intense, Self-Induced Sustainable Microwave Plasma Using CNTs From $CO_2$ FIG. 3 shows a series of photographs of a brilliant plasma that arises in three repeat runs of a 1 of the carbanogel sample in an Erlenmeyer flask irradiated at 2.45 GHz in a E3280 microwave oven at 3020 W irradiation. Note, that the CNT is heated by the microwave and triggers the plasma at 3 s (see the fourth panel from the left in the top row of FIG. 3) that is then continuous throughout the 1-min microwave exposure time. As shown in the top right panel of FIG. 3, the plasma spontaneously extinguishes at the end when the microwave field is turned off. Each run is at 3000 W in the NE3280 microwave. The complete videos are seen in videos posted at: (https://www.youtube.com/watch?app=desktop&v=GRzeSMIZI_c&feature=youtu.be) Movie 1, (https://www.youtube.com/watch?app=desktop&v=1zqAYVEmFX0&feature=youtu.be) Movie 2, and (https://www.youtube.com/shorts/MbUHwm0ikLY?app=desktop) Movie 3.

The carbanogel used in the images of FIG. 3 were synthesized from 5% $CO_2$ flue gas. The flue gas was electrolyzed in 770° C. molten $Li_2CO_3$ for 17 hours at 2800 A on a 6,232 $cm^2$ cathode (an electrolysis current density J=0.45 $A/cm^2$). This is a cathode comparable in shape and composition, but larger, than the post-electrolysis cathode shown in FIG. 2, panel D. The cathode was positioned across from a 304 Stainless Steel electrode serving as both the anode and as the cell case. Post electrolysis, the electrolysis carbanogel product was collected from the cathode, excess electrolyte removed, HCl washed, and (pre-) characterized with TGA.

In each microwave exposure, as exemplified in the top row of FIG. 3, the CNT containing carbanogel triggered a continuous, sustained, spatially constrained, undulating, bright yellow-white plasma throughout the 1 minute of applied microwave irradiation. In the first few seconds, the sample turns partially red with microwave heating, followed in the next second by induction and triggering of a continuous plasma. In the movies, the plasma is accompanied by an audible 120 Hz hum presumably related to variation of the applied microwave field.

The bottom row of FIG. 3 shows images of the sample with the microwave-driven plasma, and then with the flask removed from the microwave at the end of each of the three runs. In each image, the plasma was sustained at a uniform, undulating intensity throughout. The sample in the flask remained intact after the first and second runs. Note, that the sample remained partially red hot (cooling ~3 s) after the microwave irradiation was terminated. The remains were substantially intact after the first and second runs. The plasma began to soften the borosilicate flask by the end of the second run (see Movie 2), and the softened flask collapsed due to the plasma heat by the end of the third run (see Movie 3). This established a lower limit to the plasma temperature as the 820° C. softening temperature of the borosilicate 7740 Pyrex glass used.

A variety of other GNCs samples were also irradiated for 1 min, but at a five-fold lower power of 650 W in a Toshiba 201 Laboratory Microwave, rather than in the NE-3280. As seen in Movie 4 (https://www.youtube.com/watch?app=desktop&v=rosw5xtymHg&feature=youtu.be). A consistently intense plasma is again observed, emanating from the sample within an open Pyrex beaker. About 1 g of the CNT used in FIG. 3 triggered, and again sustained, this bright plasma. The CNTs were observed to require a longer plasma trigger time of about 10 s, rather than the about 2 s observed when using the higher power microwave oven.

The same sustained plasmas were reproducibly observed in three additional CNTs containing carbanogel samples. Each of the CNT containing carbanogel samples were synthesized in separate 16-hour electrolysis of $CO_2$ in 770° C. $Li_2CO_3$, each at a current density of J=0.6 A/cm$^2$, and using Muntz Brass cathodes and 304 Stainless Steel anodes. Each was prepared with $CO_2$ from the flue gas of the Shepard natural gas power plant in Calgary, Canada. The first sample was analyzed and shown to have 95% SEM CNT purity and TGA CNT purity. The second sample had 90% SEM CNT purity and 97% TGA CNT purity. The third sample had 95% SEM CNT purity and 97% TGA CNT purity. As with the first sample, each of the 3 samples chosen from an inventory of in-house CNTs, when exposed to under 1-minute of a 650 W microwave field, reliably triggered a bright, continuous plasma.

A fascinating phenomenon was observed (shown in Movie 5: https://www.youtube.com/watch?app=desktop&v=wsdw5TalMfg&feature=youtu.be), in a second run, following the run shown in Movie 4, of the lower power 650 W microwave irradiation of an in-house CNT sample—made from $CO_2$—in a beaker. In this case, the triggering of the plasma split the beaker, and the plasma escaped intact, and migrated intact to the top of the microwave where it continued as a bright, continuous oval-shaped plasma throughout the full minute of irradiation, only extinguishing when the microwave radiation field was turned off. Stainless steel 304 (SS 304) is resistant to oxidation to 925° C., and the lack of oxidation as the microwave SS 304 ceiling establishes this maximum temperature of the plasma. Hence the plasma, which can soften borosilicate is within the temperature range of 820-925° C.

Without being bound by any particular theory, the plasma generated by exposing GNCs generated from the electrolytic splitting of $CO_2$ in a molten carbonate electrolyte may resemble the plasma generated by the observed plasmas a coaxial waveguide device, also referred to as a "microwave drill bit". This coaxial waveguide device consists of a cylinder with an inner conductive antenna, which can be lowered to make contact with a material. The coaxial waveguide contains a moving central macroscopic electrode antenna, that acts to direct input microwave radiation to induce molten hot spots at the point of contact with various materials, such as: germanium, alumina, NaCl, Si, Cu, basalt, or other materials. This releases airborne particles of those materials ranging from 10 nm to several microns in size. These particles act as partially ionized emitters in a "dusty plasma" sustained fireball. A feature of the fireballs is the tendency to spontaneously adapt its shape to absorb most of the transmitted microwave energy. The optical emission spectrum of the fireballs is in accord with the originating material (copper hot spots exhibit characteristic emission spectrum of copper, NaCl exhibits characteristic emission spectrum of sodium, Si exhibits characteristic emission spectrum of silicon, and Cs powder on glass exhibit both the Si and Cs characteristic emission spectra).

Herein it was observed generation of a similar plasma, triggered with nanoparticles and without a coaxial waveguide. In particular, multi-walled CNTs (MWCNTs) made from $CO_2$, appear to act as a channel of microwave energy, creating multiple hot spots, and directly inducing a plasma fireball without the need for a macroscopic device with moveable antenna specifically placed within a coaxial waveguide. Without being bound by any particular theory, it may be that the physical chemical properties of MWCNT—as compared to single walled CNTs (SWCNTs)—contribute to this observed phenomenon. Also, the specific physical chemical differences between GNCs synthesized from $CO_2$ and carbon nanotubes synthesized by other means, such as chemical vapor deposition (CVD).

Fundamental advantages of MWCNT compared to SWCNT to trigger and sustain microwave-driven-plasmas. Multi-Walled CNTS (MWCNTs), compared to Single-Walled CNTs (SWCNTs) generate a narrow emission band, promoting more constructive interference driving a better plasma yield. MWCNTs may broaden the wavelength of EM (microwave) absorptivity compared to SWCNT, as different diameter CNT absorb different wavelengths and again principally by narrowing the emission band and redistributing energy as a skin effect through the expanded surface of the MWCNT.

MWCNTs exhibit greater rigidity than SWCNTs increasing retention of morphology under harsh (plasma) conditions. Similarly, the lifetime of MWCNTs can be enhanced if outer MWCNT layers are corroded off (during plasma emission), while the integrity of inner layers is maintained.5 MWCNT generally facilitates metallic, rather than semimetallic, or semiconductor conductivity compared to SWCNTs, as only certain levels of configurations and larger diameters of SWCNT are metallic.

Interactions between MWCNT layers can promote electron and hole mobility enhancing microwave absorption. The higher degree of metallic nature of the MWCNTs facilitates electrons to migrate more readily from one CNT bundle to another or to layers within an individual. Plasma-induced electron or hole loss from MWCNTs, will have a lower impact on the MWCNTs themselves as they can sustain higher currents. The rigidity, larger carbon resource, and higher sustained currents of MWCNTs may promote better ongoing reductive healing, by localized plasma containing carbon species, of chemical and oxidative defects due to plasma corrosion better than SWCNTs. MWCNTs are less likely to break at defects than SWCNTs. The higher density, and individual particle mass, of MWCNTs may provide a barrier to their being displaced by plasmas. As with electronic conduction, MWCNTs maintain a high total heat capacity and support more thermal vibration modes, to radiate and dissipate surface energy.

Plasma-Advantaged Properties of CNTs From $CO_2$

CNTs prepared by the molten carbonate electrolytic splitting of $CO_2$ present several unique characteristics that appear to be advantageous to plasma generation, when exposed to a field of microwave radiation, compared to CNTs synthesized by conventional methods (such as CVD and arc ablation methodologies). Molten carbonate splitting of $CO_2$ prepared CNTs may be magnetic and retain a higher metal or metal carbide content which can promote electron mobility. CNTs prepared by molten carbonate splitting of $CO_2$ may be longer than conventionally synthesized CNTs and that increased length may conduct better, support more robust structures physically, and support more vibrational modes. Thicker, MWCNTs may have the advantage of carrying higher current capacity, skin effect, and absorptivity advantages, being more physically and chemically robust, positive electron emitting promoting with hole conduction properties, with improved thermal conduction, and being more metallic. Also, the molten carbonate splitting of $CO_2$ prepared CNTs may have unique micro to macro structures as they are derived from carbanogel with CNT aggregates that may increase absorptivity or entrapment of microwaves, ions, free-electrons, heat, and gases. Without being bound by any particular theory, metallic impurities in the molten carbonate splitting of $CO_2$ prepared CNTs may: (i) increase electrons or holes available for the CNT to conduct or use, (ii) may increase the conductivity by bridging gaps, (iii) act as catalyst particles for the splitting of molecules, (iv) help CNT regeneration, (v) increase magnetic interaction with the magnetic component of EM field (which would increase absorptivity), and (v) under stress may retain CNT structural integrity, and permit a transfer of charges. Gases absorbed prior to plasma ignition may act as a start source for the plasma, as they are nearer to the surface of the CNT so energy is more easily transferred to them.

CNT-Induced Microwave-Plasma Self-Purification of CNTs

One application of the efficient, spatially constrained CNT-induced microwave-driven plasma is purification of the molten carbonate splitting of $CO_2$ prepared CNTs. Purification may be accomplished with one to two orders of magnitude lower plasma power or time than a conventional bench-top plasma designed for cleaning. Without purification, molten carbonate CNTs synthesized by $CO_2$ splitting may retain, post-electrolysis impurities, consisting of metals, electrolyte, and amorphous carbons that can be significantly removed by plasma treatment and washing. The plasma can expose and/or oxidize impurities, and the washing can remove solid plasma purification products (those that were not volatilized during the plasma application).

Figure 4:
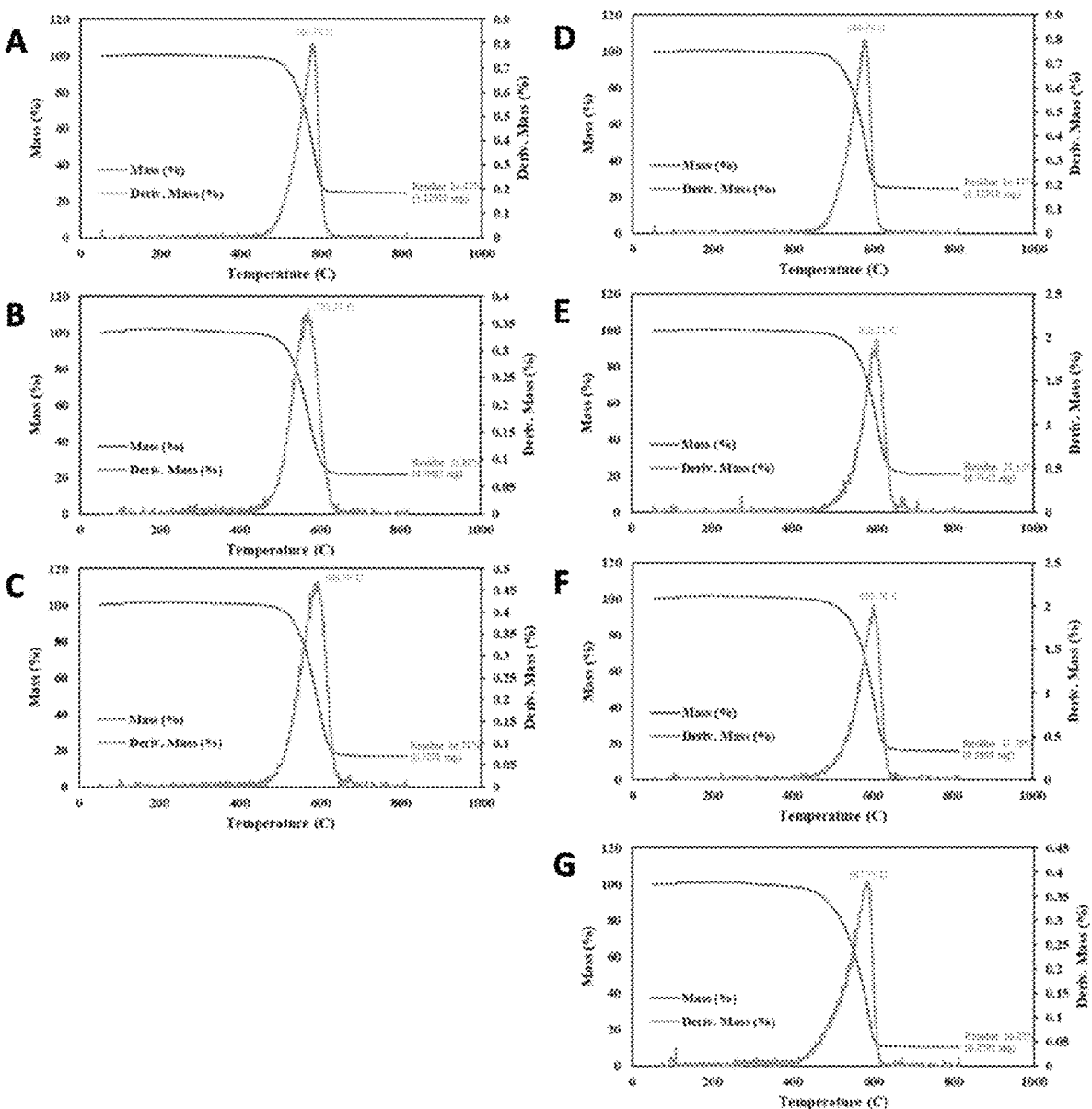
FIG. 4 shows the results of thermogravimetric analysis (TGA) of various GNC products.

FIG. 4 shows the TGA results of a molten carbonate splitting of $CO_2$ CNT product before, and after, various plasma treatments. The product was synthesized with a 780° C. $Li_2CO_3$ 3-hour electrolysis, conducted at J=0.2 A/cm² with a stainless steel 304 anode at an 840 A/cm² area brass cathode. FIG. 4 panel A and panel D show the TGA results of the extracted, washed CNT product prior to plasma purification content. FIG. 4 panel B and panel C show the TGA results of the CNT product after 1 hour (panel B) or 4 hours (panel C) of conventional plasma cleaning and wash in 80%/20% $HCl/H_2O_2$ at 95° C. for 4 hours. FIG. 4 panel E to panel G show the TGA results of the CNT product instead after CNT-induced microwave-driven plasma at powers of either 340 W (panel E), 3200 W (panel F), or 650 W (panel F), and washed with either 80%/20% $HCl/H_2O_2$ (panel E and panel F) or 64%/16%/20% $HCl/HNO_3/H_2O_2$ (panel G) at 95° C. for 4 hours.

In order to enhance the reliability of the purity improvements, an initial molten carbonate splitting of $CO_2$ prepared CNT product with high impurity levels was chosen as shown in TGA FIG. 4A and repeated in FIG. 4D. For purification experiments, the product was prepared with $CO_2$ directly from the air, with an 840 cm² brass electrode, electrolytically split for 3 hours at a current density of J=0.2 A/cm² in 780° C. $Li_2CO_3$. Useful measures of the CNT product impurity are the TGA mass % of the product at 800° C. and the TGA inflection temperature, $TGA_{infl}$.

As can be seen in each of the TGA presented in FIG. 4, the mass reduction with heating falls to a plateau at T>700° C. In the case of FIG. 4A resulted in a TGA measured purity of about 75.5% (100%—the measured residue). The 24.5% TGA residual mass, was comprised approximately a third of oxygen mass accumulated during heating under air. This accumulated as an oxide formed during the combustion process. Hence, the actual TGA residue was approximately 16%, and the purity was approximately $TGA_{actual}$=84%. The inflection temperature is a measure of the product's resistance to oxidation and amorphous carbon typically exhibits $TGA_{infl}$=~300° C., while a higher quality graphene nanocarbons exhibits $TGA_{infl}$>~580° C., and in this case, FIG. 4A panel, $TGA_{infl}$=571° C.

A decrease of impurities within the CNT product was probed by a lowering of the >700° C. plateau in the blue curve of the TGA, and a shift to the right of $T_{infl}$ is indicative of greater oxidation resistance. The FIG. 4A CNT sample was placed in a standard air plasma cleaner at maximum power (300 W) for 1-hour and then washed with 80%/20% $HCl/H_2O_2$ at 95° C. for 4 hours. This combined wash was more effective than either or HCl or $H_2O_2$ alone, and that 95° C. is more effective than a room temperature wash. As shown in FIG. 4B, this increased the $TGA_{measured}$ to 78.2%, although $T_{infl}$ decreased to 571° C. However, as seen with an increase to 4 hours of plasma treatment (see FIG. 4C), followed by the same post-plasma wash, the CNT purity improved with $TGA_{measured}$ to 83.3%, and $T_{infl}$ increased to 589° C. and SEM purity from 80% to 85%. Without the wash, some plasma treated impurities remained on the CNTs. For example (not shown in FIG. 4), unwashed 4-hour plasma values respectively had $TGA_{measured}$=75.5%, and $T_{infl}$=583° C.

The CNT-induced microwave-driven plasma purified CNTs more quickly and with less energy than a conventional plasma. Rather than a conventional plasma cleaning process in which the plasma is formed throughout the cleaning chamber, the CNT made from splitting $CO_2$ induced microwave-driven plasma forms that were spatially constrained at the point of cleaning. A result is that the same degree of CNT plasma purification occurred with an order of magnitude less power and/or time.

As shown in FIG. 4E, a 340 W CNT-induced microwave driven plasma produced the same extent of purification ($TGA_{measured}$=78.9%) occurred in 1 minute as 1 hour of the conventional 300W applied plasma (using the same post-washing conditions), and resulted in an increase in $T_{infl}$ to 610° C. As shown in FIG. 4F, a similar, but higher powered, 3200 W microwave plasma produced greater purification ($TGA_{measured}$=84.3%) occurred in 1 minute than 4-hours of the conventional 300 W plasma, with a good, but lower, $Ti_{infl}$=604° C. An excess of plasma treatment may continue to lower the residual impurity, but also may be detrimental to the CNT $T_{infl}$.

Intermediate levels of microwave irradiation, either 650 W or 1600 W of CNT-induced microwave driven plasma, resulted in intermediate increases in CNT purity respectively of $TGA_{measured}$=81.1% and 83.0%. As with the 340 W purification, 650 W 1 minute of microwave irradiation appeared to be less aggressive than the 3200 W purification treatment, resulting in a higher $T_{infl}$=620° C., albeit achieving a lower level of impurity removal with $TGA_{measured}$=81.1% than the 3200 W purification treatment.

As shown in Table 1 below, alternative post microwave washes than the 80%/20% $HCl/H_2O_2$ have been investigated. A nitric acid clean of the 650 W irradiated CNTs results in modestly improved impurity decrease, but is more aggressive with lower $T_{infl}$ improvements. However as seen in FIG. 4G, a 64%/16%/20% $HCl/HNO_3/H_2O_2$ post microwave wash at 95° C. for 4 hours, further decreased TGA measured impurities resulting in $TGA_{measured}$=89.8%, with a drop in $T_{infl}$=588° C.

Figure 5:
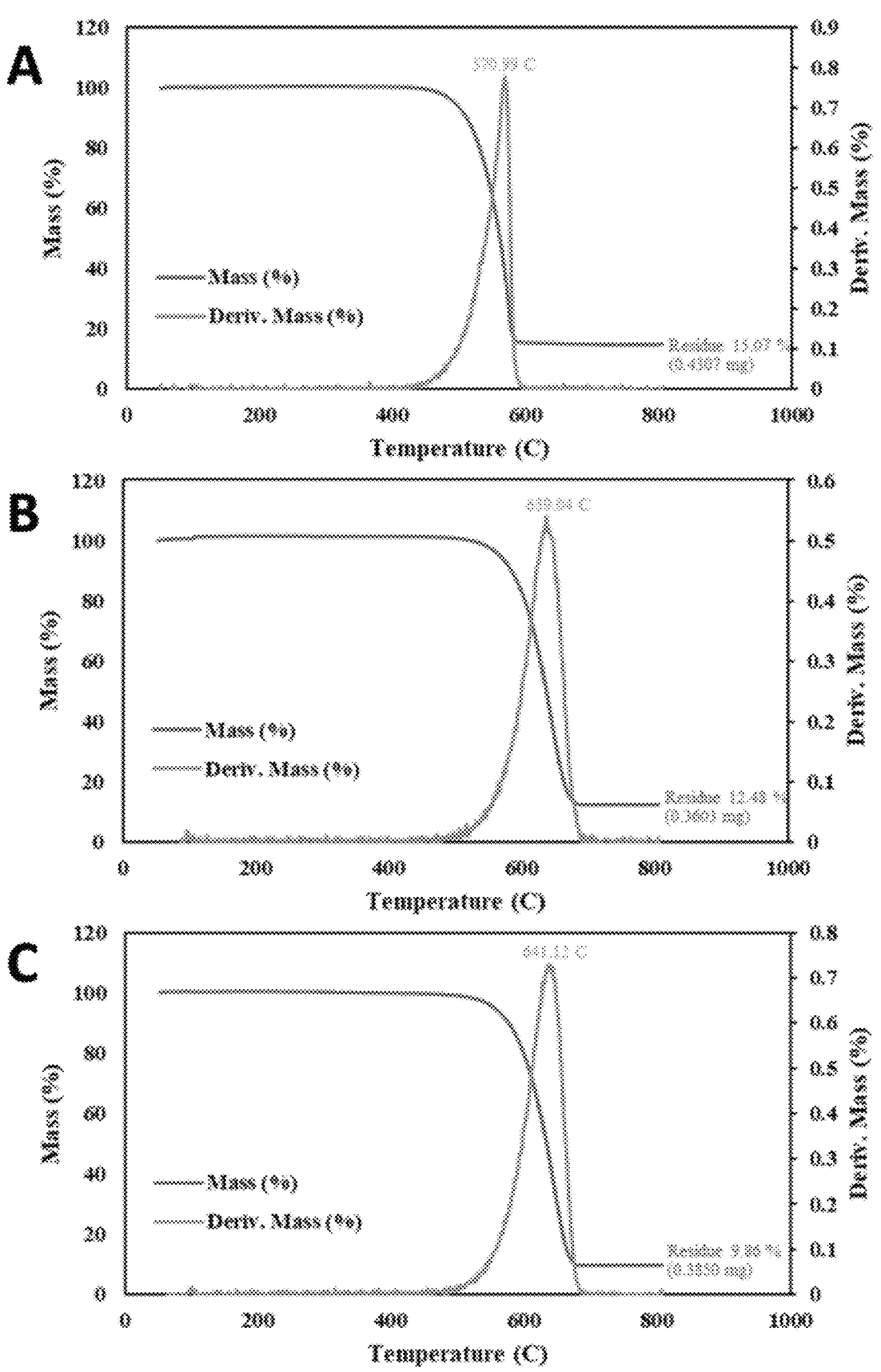
FIG. 5 shows the results of TGA of various GNC products.

Starting with a higher base purity sample of $TGA_{measured}$=84.9% rather than 75.4% in the previous example, 1 minute of reduced power CNT-induced microwave-plasma, coupled with an extend wash time further improved the CNT as summarized in FIG. 5.

FIG. 5 shows TGA results from a CNT product synthesized from molten carbonate splitting of $CO_2$ product before, and after, various plasma treatments. The product is from a 770° C. $Li_2CO_3$ 16-hour electrolysis process conducted at J=0.2/cm² with a stainless steel 304 anode at a 1020 cm² area brass cathode. FIG. 5A shows TGA results of the extracted, washed CNT product prior to plasma purification content. FIG. 5B and FIG. 5C show the TGA results of the CNT product after exposure to the CNT-induced microwave-driven plasma and washing in 75%/25% HCl/H₂O₂. FIG. 5B shows the TGA results subsequent to 650 W applied microwave with a 1-hour wash. FIG. 5C shows the TGA results subsequent to a 325 W applied microwave field with a 24-hour wash. Specifically, compared to the new base sample, the exposure to one minute of 650 W CNT-induced microwave plasma with 1 hour of 75%/25% HCl/H₂O₂ resulted in $TGA_{measured}$=87.5.2% and $T_{infl}$=639° C., compared to 325 W of microwave power and 24 hours with the same post wash yielding an improved of $TGA_{measured}$=90.1% and $T_{infl}$=641° C.

With a higher base purity sample of $TGA_{measured}$=89.7%, 4 hours of conventional 300 W plasma cleaning was again outperformed by 1 minute of cleaning with exposure to a 650 W CNT-induced microwave-plasma as summarized in FIG. 5. Specifically, compared to the base sample, the 4-hour plasma increased $TGA_{measured}$ to 93.8% and increase of $T_{infl}$ from 614 to 620° C. (again with a 4 hour 95° C. 80%/20% HCl/H₂O₂ post wash). The one minute of CNT-induced microwave plasma with the same post wash, exhibited an improved $TGA_{measured}$=95.2% and a $T_{infl}$=668° C.

TABLE 1

The purity change in CNTs made by molten carbonate electrolytic splitting of CO₂, with wash by either a conventional air (standard) plasma or a CNT-induced microwave-driven (MW) plasma, and with various post plasma-exposure washings. All post-plasma washings are conducted for 4-hours at 95° C. The label "pre" refers to a pre-plasma wash in HCl. The label "A" refers to a wash in an 80%/20% HCl/H₂O₂ mixture. Labels "B", "C" and "D" respectively refer to 80%/20%, 50%/50% or 20%/80% HNO₃/HCl mixtures. Labels "E", "F", and "G" respectively refer to 40%/40%/20%, 64%/16%/20% or 16%/64%/20% HNO₃/HCl/H₂O₂ mixture.

| CNT from CO₂ sample | Wash | TGA % | $T_{infl}$° C. |
|---|---|---|---|
| Base CNT | pre | 75.4 | 581 |
| 4 hr 300 W standard plasma | none | 75.5 | 583 |
| 4 hr 300 W standard plasma | A | 83.3 | 589 |
| 1 hr 300 W standard plasma | A | 78.2 | 571 |
| 1 min 3200 W MW plasma | A | 84.3 | 603 |
| 1 min 1600 W MW plasma | A | 83.0 | 599 |
| 1 min 650 W MW plasma | A | 81.1 | 620 |
| 1 min 340 W MW plasma | A | 78.9 | 610 |
| 1 min 650 W MW plasma | HNO₃ | 81.8 | 615 |
| 1 min 650 W MW plasma | B | 78.5 | 593 |
| 1 min 650 W MW plasma | C | 77.4 | 610 |
| 1 min 650 W MW plasma | D | 83.0 | 590 |
| 1 min 650 W MW plasma | E | 89.8 | 573 |
| 1 min 650 W MW plasma | F | 88.7 | 579 |
| 1 min 650 W MW plasma | G | 89.8 | 588 |

Figure 6:
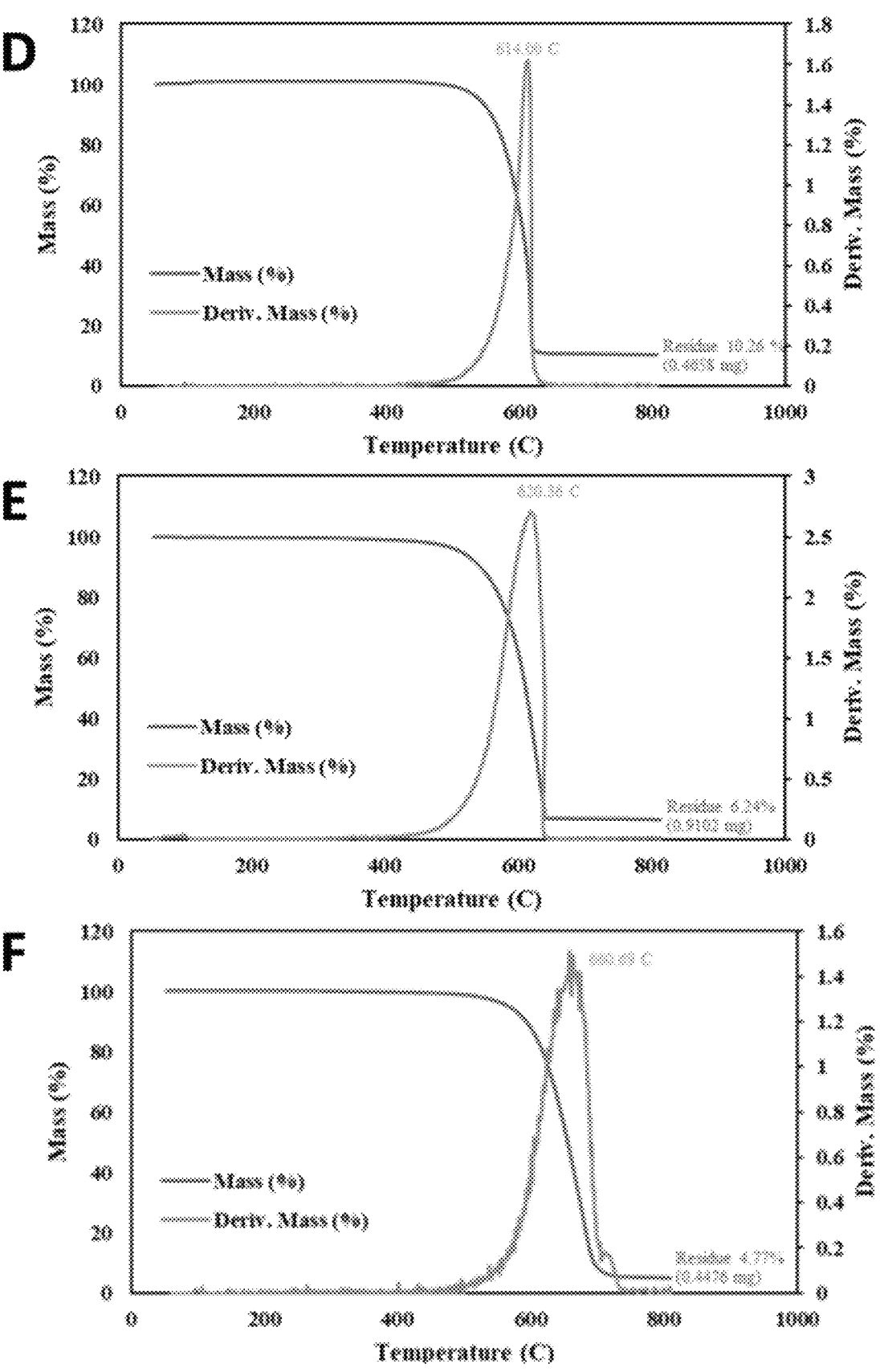
FIG. 6 shows the results of TGA of various GNC products.

FIG. 6 shows the TGA results of a CNT product made from carbonate electrolytic splitting of CO₂ before, and after, various plasma treatments. The CNT product was made in a 770° C. Li₂CO₃ 18 hour electrolysis process that was conducted at J=0.4 A/cm² with a stainless steel 304 anode at a 663 cm² area brass cathode. FIG. 6D shows the TGA results of the extracted, washed CNT product prior to exposure to plasma purification. FIG. 6E shows the TGA results of the CNT product after 4 hours of conventional plasma cleaning and wash in 75%/25% HCl/H₂O₂. FIG. 6F shows the TGA results of the CNT product after exposure to CNT-induced microwave driven plasma at powers of 650 W and washed similarly.

Figure 7:
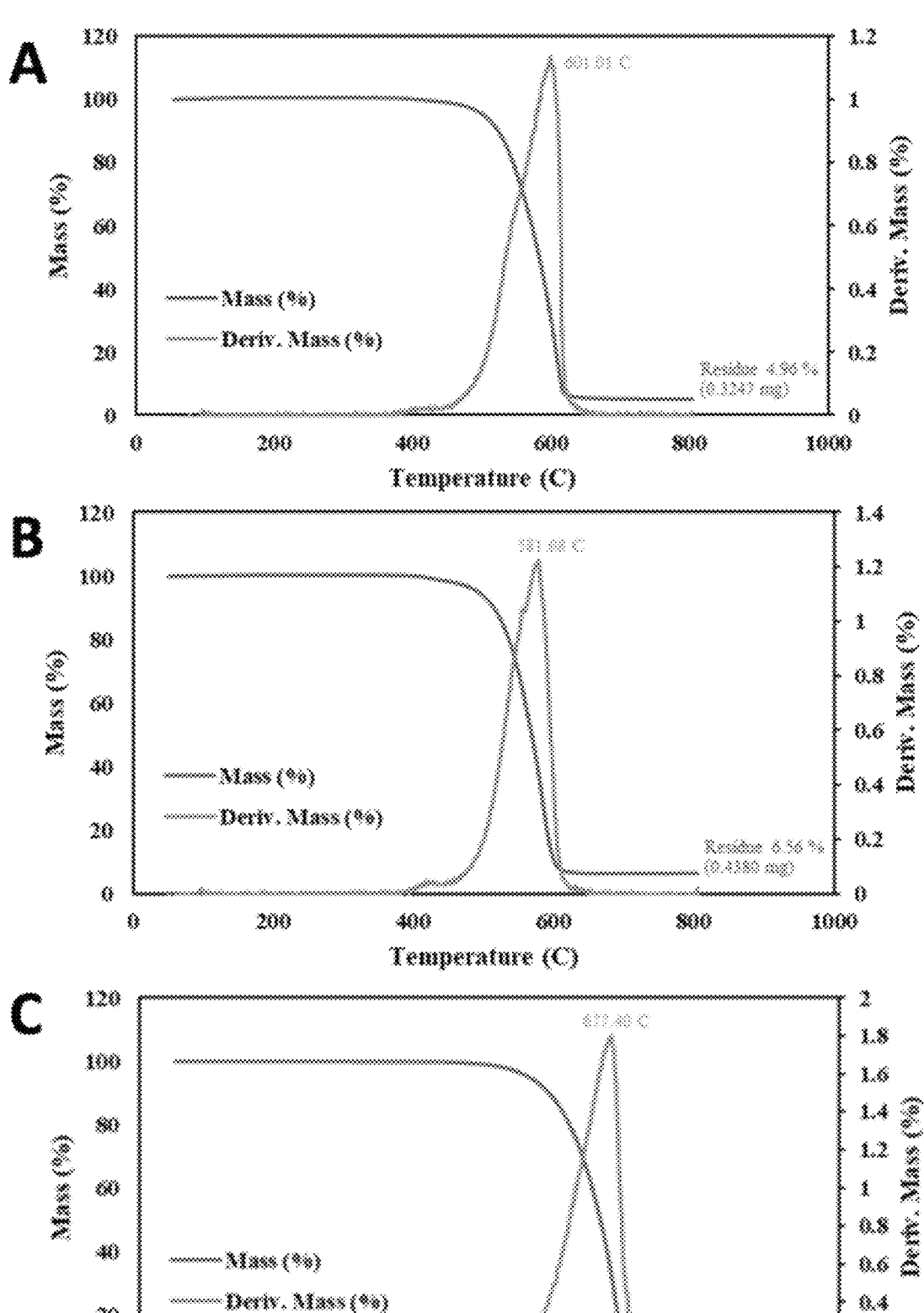
FIG. 7 shows the results of TGA of various GNC products.

A higher base purity sample of $TGA_{measured}$=95.0% and $T_{infl}$=614° C., required higher power coupled with lower irradiation time to achieve the highest purity, as shown in FIG. 7. FIG. 7 shows the TGA results of a CNT product made from carbonate electrolytic splitting of CO₂ before, and after, various plasma treatments. The CNT product was made in a 770° C. Li₂CO₃ 18-hour electrolysis process conducted at J=0.4/cm² with a stainless steel 304 anode at a 663 cm² area brass cathode. FIG. 7A shows the TGA results of the extracted, washed CNT product prior to plasma purification content. FIG. 7B shows the TGA results of the CNT product after 4 hours of conventional plasma cleaning and wash in 75%/25% HCl/H₂O₂. FIG. 7C shows the TGA results of the CNT product after CNT-induced microwave-driven plasma at powers of 650 W and similarly washed.

Exposure to 10 minute of 325 W CNT-induced microwave-plasma with an HCl wash was outperformed by 1 min at 650 W power, again followed by an HCl wash. Compared to the base sample, the 10-minute CNT-induced microwave-plasma over-powered the sample decreasing the $TGA_{measured}$ to 93.8%, although $T_{infl}$ improved to 620 C. Better was the one minute of CNT-induced microwave plasma at twice the power, exhibiting $TGA_{measured}$=96.7%, $TGA_{actual}$=97.8%, and $T_{infl}$=667° C.

Purification of CNTs From CO₂ Prepared With Low Lithium Carbonate Electrolytes

Strontium carbonate (SrCO₃) is more prevalent, and an order of magnitude less expensive, than lithium carbonate (Li₂CO₃). Economically, SrCO₃ does not face the same present-day demand issues as lithium carbonate. Hence, CO₂ decarbonization via molten carbonate electrolysis can be less expensive in Sr, rather than Li, based carbonate electrolytes. Strontium carbonate has a higher melting point (mp 1494° C.) than Li₂CO₃ (mp 723 C). However, binary, ternary, quaternary, quinary, senary, etc. salt mixtures containing high fractions of SrCO₃ can melt in the 600° C. to 800° C. temperature range. This temperature range is useful to split and transform CO₂ to GNCs by electrolysis. As with Li₂CO₃, SrCO₃ based electrolytes can produce high-quality GNCs via splitting CO₂ by electrolysis.

As shown in Table 2, SrCO₃ is several orders of magnitude less water soluble than Li₂CO₃. Hence, a SrCO₃ electrolyte impurity retained with a GNC electrolysis has the potential to be more persistent than a retained Li₂CO₃ retained impurity. This can require alternative washes to remove a more persistent electrolyte, which otherwise can be retained in the GNC product. Alternative acid washes can be more effective in separating the GNC product from the strontium-based electrolysis electrolytes. Acids with strontium salts that are more water-soluble are useful and are compared in Table 2. After the respective lithium and strontium carbonate impurities, the subsequent rows in the table compare the lithium and strontium salt solubilities of strong acid washes of hydrochloric, nitric or perchloric acid, while the last rows compare the lithium and strontium salt solubilities of weak acid washes of formic acid (H₂CO₂) or acetic acid (H₄C₂O₂) washes.

As shown in Table 2, the weaker acids have a lower washed salt solubility than the strong acids, particularly at higher temperatures. Additionally, the weaker acids are less active to remove amorphous carbon or metal impurities than the strong acids. As tested, the weaker acids dissolved and washed both lithium and strontium carbonate, but the strong acids were more effective. Both strontium chloride and strontium nitrate, as salts of HCl and nitric acid washes, are soluble, and in particular, the solubility of strontium nitrate increased more rapidly than strontium chloride with higher temperature washes. The high solubilities of the strontium salt ($Sr_2(ClO_4)_2$) of a perchloric acid wash stood out, although at higher temperatures perchloric acid is highly oxidizing which exposed the possibility that a too strong, too long, or too hot a perchloric acid wash to remove excess strontium carbonate residue has the potential to compromise the GNC quality.

on a 1,804 $cm^2$ cathode (applying an electrolysis current density J=0.6 $A/cm^2$). As shown in Table 3, a 95° C. acid wash with either $HNO_3$ or HCl resulted in a comparable TGA %, but the $HNO_3$ resulted in a moderately improved oxidation resistance ($T_{infl}$=584° C. compared to 558° C. after the HCl wash). Exposure to a 1 minute 650 W microwave

TABLE 2

The aqueous solubility of various lithium compared to strontium salts as a function of temperature. The aqueous solubility expressed in g/100 ml water is S(T ° C.). The aqueous solubility expressed in molality, moles salt/kg water is $S_m$(T ° C.). Non-carbonate salts are salts of the strong acids HCl, $HNO_3$, and $HClO_4$, or in the latter rows, respectively of acetic or formic acid washes.

| Salt | S(0°) | S(10°) | S(20°) | $S_m$(20°) | S(30°) | S(40°) | S(60°) | S(80°) | S(90°) | S(100°) |
|---|---|---|---|---|---|---|---|---|---|---|
| $Li_2CO_3$ | 1.54 | 1.43 | 1.33 | 0.18 | 1.26 | 1.17 | 1.01 | 0.85 | | 0.72 |
| $SrCO_3$ | | | 0.0011 | 2.4E−04 | | | | | | 0.065 |
| LiCl | 69.2 | 74.5 | 83.5 | 19.7 | 86.2 | 89.8 | 98.4 | 112 | 121 | 128 |
| $SrCl_2$ | 43.5 | 47.7 | 52.9 | 2.3 | 58.7 | 65.3 | 81.8 | 90.5 | | 101 |
| $LiNO_3$ | 53.4 | 60.8 | 70.1 | 10.2 | 138 | 152 | 175 | | | |
| $Sr_2(NO_3)_2$ | 39.5 | 54.9 | 10 | 3.3 | 87.6 | 91.3 | 94.0 | 99.0 | 101.1 | |
| $LiClO_4$ | 42.7 | 49 | 56.1 | 5.3 | 63.6 | 72.3 | 92.3 | 128 | 151 | |
| $Sr(ClO_4)_2$ | 233.8 | 258.7 | 291.7 | 10.2 | 327.5 | 363.9 | | | | |
| LiHCO2 | 32.3 | 35.7 | 39.3 | 7.6 | 44.1 | 49.5 | 64.7 | 92.7 | 116 | 138 |
| Sr(HCO2)2 | 9.1 | 10.6 | 12.7 | 0.7 | 15.2 | 17.8 | 25 | 31.9 | 32.9 | 34.4 |
| LiC2H3O2 | 31.2 | 35.1 | 40.8 | 5.6 | 50.6 | 68.6 | | | | |
| Sr(C2H3O2)2 | 37 | 42.9 | 41.1 | 1.6 | 39.5 | 38.3 | 36.8 | 36.1 | 36.2 | 36.4 |

Table 3 shows the results of comparing a high concentration strontium electrolyte CNT products, the $TGA_{measured}$ purity (TGA %), and the inflection temperature, $T_{infl}$° C. subsequent to different strong acid treatments that were employed to remove residue and improve the purity of the CNT product. The table includes product purification of two separate high strontium carbonate electrolytes. The first electrolysis was conducted at 770° C. in a molten 65 wt % $SrCO_3$, 35 wt % $Li_2CO_3$ electrolyte for 16 hours at 1082 A treatment of the $HNO_3$ washed product, followed by washing again in 95° C. $HNO_3$, increased the TGA % from 87.5% to 92.3% and $T_{infl}$ from 584 to 599° C. When in the 95° C. $HNO_3$ post wash was replaced with a 95° C. post wash mix of 40% HCl, 40% $HNO_3$ and 20% $H_2O_2$, TGA and $T_{infl}$ further improved to 93.1° C. and 609° C. This post wash of acid and $H_2O_2$ mix was also effective in improving the HCl prewashed product.

TABLE 3

Summarizes purity improvement data with post electrolysis treatments for CNTs made by $CO_2$ splitting in a high strontium carbonate content electrolyte. The electrolyte was either % Sr = 65 (60/35 wt % $SrCO_3$/$Li_2CO_3$) or % Sr = 50 (50/50 wt % $SrCO_3$/$Li_2CO_3$). The CNT product was with washed with various strong acids or acid mixtures, as indicated. Some products, as listed, are both washed, and also purified with a conventional air (standard) plasma or by exposure to a CNT-induced microwave-driven (MW) plasma. Subsequent to the various plasma treatments, the CNT product was also post washed as indicated. The "post mix" consisted of a 4 hour wash with 40% HCl, 40% $HNO_3$ and 20% $H_2O_2$ (by volume at 95° C.).

| % Sr | Acid Wash | Post treatment | Temperature | TGA % | $T_{infl}$° C. |
|---|---|---|---|---|---|
| 65 | $HNO_3$ | — (none) | 95° C. | 87.5 | 584 |
| 65 | $HNO_3$ (pre&post) | 650 W microwave, 1 minute | 95° C., pre&post microwave wash | 92.3 | 599 |
| 65 | HCl | — (none) | 95° C. | 87.6 | 558 |
| 65 | Pre HCl/post mix | 650 W microwave, 1 minute | 95° C., pre&post microwave wash | 91.5 | 606 |
| 65 | pre $HNO_3$/post mix | 650 W microwave, 1 minute | 95° C., pre&post microwave wash | 93.1 | 609 |
| 50 | no wash | — (none) | — | 84.5 | 529 |
| 50 | HCl | — | room temperature, RT | 86.7 | 525 |
| 50 | HCl | 650 W microwave, 1 minute | RT, pre & post microwave wash | 93.9 | 621 |
| 50 | HCl | 300 W plasma, 4 hours | RT, pre & post plasma wash | 92.5 | 602 |
| 50 | HCl | — (none) | 35° C. | 90.6 | 589 |
| 50 | $HClO_4$ | — (none) | 60° C. | 90.7 | 620 |
| 50 | $HClO_4$ | — | 95° C. | 95.7 | 517 |
| 50 | HCl | — | 95° C. | 90.7 | 609 |
| 50 | $HNO_3$ | — | 95° C. | 93.4 | 622 |

TABLE 3-continued

Summarizes purity improvement data with post electrolysis treatments for CNTs made by
$CO_2$ splitting in a high strontium carbonate content electrolyte. The electrolyte was either %
Sr = 65 (60/35 wt % $SrCO_3$/$Li_2CO_3$) or % Sr = 50 (50/50 wt % $SrCO_3$/$Li_2CO_3$.
The CNT product was with washed with various strong acids or acid mixtures, as
indicated. Some products, as listed, are both washed, and also purified with a conventional air
(standard) plasma or by exposure to a CNT-induced microwave-driven (MW) plasma. Subsequent
to the various plasma treatments, the CNT product was also post washed as indicated. The
"post mix" consisted of a 4 hour wash with 40% HCl, 40% $HNO_3$ and 20% $H_2O_2$
(by volume at 95° C.).

| % Sr | Acid Wash | Post treatment | Temperature | TGA % | $T_{infl}$ ° C. |
|---|---|---|---|---|---|
| 50 | 80/20 $HNO_3$/$HClO_4$ | — | 95° C. | 94.2 | 614 |
| 50 | 50/50 $HNO_3$/$HClO_4$ | — | 95° C. | 95.5 | 596 |
| 50 | 20/80$HNO_3$/$HClO_4$ | — | 95° C. | 96.5 | 586 |

A second electrolysis was conducted at 785° C. in a molten 50/50 wt % $SrCO_3$/$Li_2CO_3$ electrolyte for 16 hours at 958 A on a 1,5396 $cm^2$ cathode (applying an electrolysis current density J=0.6 A/$cm^2$). The product is high-purity CNTs, as determined by SEM. As shown in Table 3, with HCl the TGA % purity increased (from 86.7% to 90.7%) and $T_{infl}$ (from 525 to 609° C.) improved as the wash temperature is sequentially increased from room temperature (~22° C.) to 35-95° C. Also shown in Table 3 are results from combining exposure to a 1 minute 650 W microwave treatment and a pre and post room temperature HCl wash. The TGA purity (93.9%) and $T_{infl}$ (621° C.) were both considerably improved compared to the room temperature HCl wash alone (with the microwave purification treatment). SEM images of 6 distinct areas of the high CNT purity sample are shown in FIG. 8.

Figure 8:
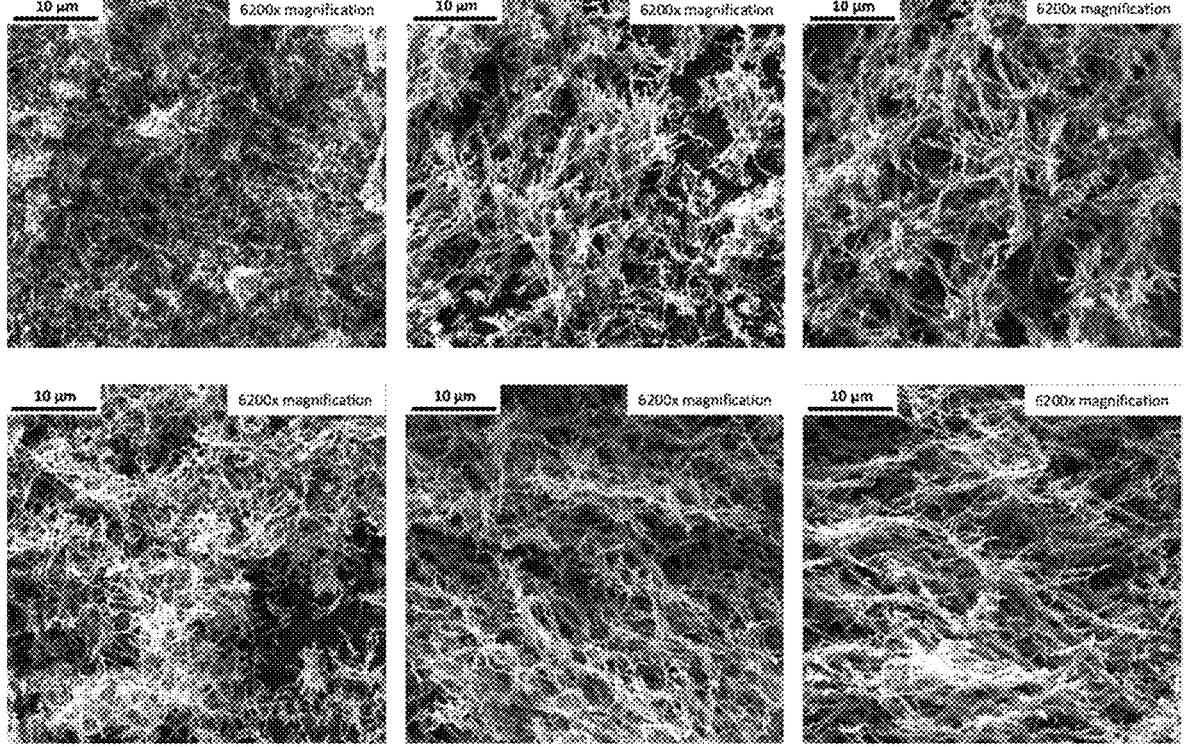
FIG. 8 shows SEM images of various GNC products.

FIG. 8 shows SEM images of a CNT product made from molten carbonate electrolytic splitting of $CO_2$ using a high $SrCO_3$ content carbonate electrolyte before, and after, one minute of exposure to a 650 W microwave field. Before and after the exposure, the product was washed with HCl at room temperature. The CNT product was made with a 785° C. 50 wt % $SrCO_3$/50 wt % $Li_2CO_3$ 16-hour electrolysis process conducted at J=0.6 A/$cm^2$ with a stainless steel 304 anode at a 1,596 $cm^2$ area brass cathode. Each SEM is at 6,200× magnification from distinct areas of the CNT product.

Furthermore, as shown in Table 3 once again a conventional plasma chamber purification treatment (4 hours at 300 W) does not purify as well as exposure to 1 minute of a microwave field.

In Table 3, the 60° C. perchloric acid treated product was TGA % at 90.7% which is the same as the HCl treated product, but $T_{infl}$=620° C. improves, which is indicative of a more oxidation-resistant product. With a perchloric acid wash at 95° C., the TGA purity considerably increases (95.7%), but the oxidation resistance considerably deteriorates ($T_{infl}$=517). Compared to HCl, at 95° C., the nitric acid wash provides high TGA purity (93.4%) and higher $T_{infl}$=622° C. At 95° C., with mixed nitric acid/perchloric acid washes, the TGA purity sequentially increases as the perchloric acid volume percent increases. That is, comparing 20/80, 50/50 and 80/20 wash mixes TGA % respectively further increases from 94.2%, 95.5%, and 96.5%. However, the additional perchloric acid diminishes the oxidation resistance of the product from 614° C., and 596° C. to 586° C.

Without being bound by any particular theory, the embodiments of the present disclosure relate to an intense, self-induced sustainable plasma by exposing CNTs produced from molten carbonate electrolytic splitting of $CO_2$.

The embodiments of the present disclosure offer a low-energy consumption, minimal carbon footprint, and cost-effective process for generating plasma and for purifying GNC products. Typical costs for commercial synthesis of GNCs such as CNTs, CNOs, and graphene are prohibitively high due to the substantial energy, material, and carbon emissions associated with CVD production. The molten carbonate electrolysis processes described herein require only $CO_2$ as a reactant, with electrolysis energy needs ranging from 0.8-2.0V for the transformation of $CO_2$ into useful GNC products. This results in GNC production costs being up to three orders of magnitude lower than those of CVD methods, which are typically ~$1,000/ton in bulk. This cost structure is comparable to industrial electrolytic processes that produce commercial-grade aluminum.

Current Applications of Cold/Warm Plasmas

Cold and warm plasmas are non-thermal equilibrium plasmas, including not only free ions and electrons but also species which have not been ionized. While thermal (hot) plasmas maintain a high enough thermal energy to remain in the plasma state, non-thermal plasmas require an external power source, to remain in the plasma state. Here, the borderline distinguishing cold and warm plasmas is considered to be about 800-1000° C., although the literature describes a broad range of alternative non-thermal plasma temperature ranges. This places the 850-950° C. temperature range of microwave field exposed GNC methods for generating plasma as applicable to both cold and warm plasma applications. Such non-thermal plasmas have a variety of applications, providing an energetic nature without many of the disadvantages attributed to hot plasmas. A hot plasma energy is often harder to generate, contain, and extinguish than cold or warm plasma.

Some uses of non-hot plasma are as follows: to break up or ionize material for characterization purposes, especially for ICP-MS (inductively coupled plasma-mass spectroscopy), without breaking up material too much while requiring lower energy than other methods like hot plasmas and not making more exotic species that can interfere with instruments. Non-hot plasmas may be used to disinfect a wide variety of surfaces, clean wounds from pathogens, kill cancer cells or specific cell types in vivo, promote stem cell or blood vessel growth, and promote blood flow; bond dental and other medical materials; along, with waste treatment from wastewater to sludge to pyrolysis chamber to make gasses; and food sanitation. Non-hot plasma has also been used to sterilize metal without diminishing sharpness, which is much better for items like surgical equipment or very locally hardened metal surfaces. Non-hot plasma has also been used to clean chip, metal, and textile fiber surfaces;

roughen or polish polymers or metal surfaces; surface modify numerous polymers, metals, and textiles while saving energy and lowering pollutants emitted. Non-hot plasma has also been used to make plasma shields to protect from microwave or other EM waves, reduce drag, and to act as a heat shield or a window that can be opened/closed, or accelerate or trap ions or particles, such as for generating small rocket thrust. Non-hot plasma has also been used to chemically reduce gasses.

We claim:

1. A method for generating and using plasma, the method comprising steps of:
    (a) generating a field of microwave radiation;
    (b) exposing a carbanogel to the field of microwave radiation for generating the plasma, wherein the carbanogel comprises a carbonate electrolyte and a carbon nanomaterial; and
    (c) directing the generated plasma at a material for use in cleaning, purifying, disinfecting, healing, etching, modifying, toughening, polishing, promoting flow in, decelerating, or activating the material, or any combination thereof.

2. The method of claim 1, wherein the carbon nanomaterial is a graphitic carbon nanomaterial.

3. The method of claim 1, wherein the carbon nanomaterial comprises graphene, a carbon nanotube (CNT), a carbon nanofiber (CNF), a thin-walled CNT, a carbon nanobamboo, a nano-pearl, a nano-tree, a conical CNF, a metal coated Ni-coated CNT, a nano-flower, a nano-dragon, a nano-rod, a nano-belt, a nano-onion, a hollow nano-onion, a nano-scaffold, a nano-platelet and nano-helices.

4. The method of claim 1, further comprising a step of providing the carbon nanomaterial as a product of an electrolysis process that splits carbon dioxide.

5. The method of claim 4, further comprising a step of introducing a dopant to the electrolysis process for making a doped carbon nanomaterial.

6. The method of claim 4, further comprising a step of introducing a magnetic additive component to the electrolysis process for making a magnetic carbon nanomaterial.

7. The method of claim 1, further comprising a step of directing the generated plasma at a cell.

8. The method of claim 1, further comprising a step of directing the generated plasma for making a plasma shield or a heat shield, an electromagnetic shield, a drag shield or any combination thereof.

9. The method of claim 1, further comprising a step of directing the generated plasma for accelerating, trapping, and controlling a flow of ions, a flow of particles, or any combination thereof.

10. The method of claim 1, further comprising a step of directing the generated plasma for chemically reducing a gas.

11. The method of claim 1, wherein the plasma comprises excited carbon.

12. The method of claim 1, wherein the plasma comprises excited components of glass, borosilicate glass, alumina, sodium chloride, basalt, or any combination thereof.

13. The method of claim 1, wherein the plasma comprises excited sodium, excited chlorine, excited silicon, excited copper, excited cesium, or any combination thereof.

14. The method of claim 1, wherein the plasma comprises a gas.

15. The method of claim 1, wherein the plasma comprises a cold plasma, a warm plasma or any combination thereof.

16. The method of claim 1, wherein the plasma does not generate any exotic species.

* * * * *